(12) United States Patent
Zhu et al.

(10) Patent No.: US 9,695,164 B2
(45) Date of Patent: Jul. 4, 2017

(54) CRYSTALLINE FORMS OF PYRROLOQUINOLINE QUINONE DISODIUM SALT

(71) Applicant: Zhucheng Haotian Pharm Co., Ltd., Zhucheng, Shandong (CN)

(72) Inventors: Liping Zhu, Shandong (CN); Liye Lu, Shanghai (CN); Jianrong Wang, Shanghai (CN); Linlin Sun, Shanghai (CN); Xuefeng Mei, Shanghai (CN); Jianxin Gu, Shanghai (CN)

(73) Assignee: Zhucheng Haotian Pharm Co., Ltd., Zhucheng, Shangdong Pro. (CN)

( * ) Notice: Subject to any disclaimer, the term of this patent is extended or adjusted under 35 U.S.C. 154(b) by 0 days.

(21) Appl. No.: 14/441,571

(22) PCT Filed: Sep. 10, 2013

(86) PCT No.: PCT/CN2013/083195
§ 371 (c)(1),
(2) Date: May 8, 2015

(87) PCT Pub. No.: WO2014/071772
PCT Pub. Date: May 15, 2014

(65) Prior Publication Data
US 2015/0291583 A1    Oct. 15, 2015

(30) Foreign Application Priority Data
Nov. 9, 2012  (CN) .......................... 2012 1 0452297

(51) Int. Cl.
C07D 471/04    (2006.01)

(52) U.S. Cl.
CPC ................... *C07D 471/04* (2013.01)

(58) Field of Classification Search
CPC .................................................... C07D 471/04
USPC ........................................... 546/84; 514/292
See application file for complete search history.

(56) References Cited

U.S. PATENT DOCUMENTS

| 7,279,514 B2 * | 10/2007 | Lenz .................... C08K 5/0041 |
| | | 428/480 |
| 8,088,422 B2 | 1/2012 | Gu et al. |
| 9,163,014 B2 * | 10/2015 | Edahiro ..................... A23L 1/30 |
| 9,321,770 B2 * | 4/2016 | Edahiro ..................... A23L 1/30 |
| 2012/0116087 A1 | 5/2012 | Edahiro et al. |
| 2013/0253001 A1 | 9/2013 | Ikemoto |
| 2014/0128609 A1 | 5/2014 | Ikemoto et al. |

FOREIGN PATENT DOCUMENTS

| CN | 101885725 | | 11/2010 |
| JP | 2692167 | | 9/1997 |
| JP | 2011219388 | | 11/2011 |
| JP | 2013112677 | | 6/2013 |
| WO | 2011007633 | * | 1/2011 |
| WO | 2014/0128609 | * | 5/2014 |

OTHER PUBLICATIONS

International Search Report in International Application No. PCT/CN2013/083195 dated Dec. 12, 2013.
International Patent Report on Patentability in International Application No. PCT/CN2013/083195 dated Feb. 26, 2015.
Notification of Transmittal of Translation of the International Preliminary Report on Patentability in International Application PCT/CN2013/083195 mailed Sep. 11, 2015.
Francene Steinberg et al.,"Pyrroloquinoline Quinone Improves Growth and Reproductive Performance in Mice Fed Chemically Defined Diets", Exp. Biol. Med. 228:160-166 (2003).
Killgore John et al., "Nutritional Imnportance of Pyrroloquinoline Quinone", Science 245, 4920 (1989).
Xu Qin et al. "Purification of pyrroloquinoline quinone and its therapeutic ef fect on lead poisoned mice", Chin. J. Ind. Hyg. Occup. Dis. 19(6):401-403 (2001).
Toshihiro Tsuchida et al., "The protective effect of pyrroloquinoline quinone and its derivatives against carbon tetrachloride-induced liver injury of rats", Journal of Gastroenterology and Hepatology 8, 342-347 (1993).
Li Haohuan et al., "Pyrrobquinolinequinone enhances regeneration of transected scia ticnerve in rats", Chinese Journal of Traumatology 8(4): 225-229 (2005).
Kohji Yamaguchi et al., "Stimulation of Nerve Growth Factor Production by Pyrroloquiinoline Quinone and Its Derivatives in Vitro and in Vivo", Biosci. Biotech. Biochem. 57(7): 1231-1233 (1993).
Shiqing Liu et al., "Enhanced Rat Sciatic Nerve Regeneration Through Silicon Tubes Filled With Pyrroloquinoline Quinone", Microsurgery 25:329-337 (2005).
Bo-qing Zhu et al., "Pyrroloquinoline Quinone (PQQ) Decreases Myocardial Infarct Size and Improves Cardiac Function in Rat Models of Ischemia and Ischemia/Reperfusion", Cardiovascular Drugs and Therapy 18:421-431, (2004).
Hobara et al., "Quinone derivatives lower blood and liver acetaldehyde but not ethanol concentrations following ethanol loading to rats." Pharmacology 37(4):264-7 (1988).
Jun-Jing Zhang et al., "Protective effect of pyrroloquinoline quinone against Aβ-induced neurotoxicity in human neuroblastoma SH-SY5Y cells", Neuroscience Letters 464:165-169 (2009).
Bhavani S. Shankar et al., "Role of glutathione in augmenting the anticancer activity of pyrroloquinoline quinone (PQQ)", Redox Report 15(4):146-154 (2010).

(Continued)

*Primary Examiner* — Rita Desai
(74) *Attorney, Agent, or Firm* — Greenberg Traurig, LLP; Fang Xie

(57) ABSTRACT

The present invention relates to crystalline forms of pyrroloquinoline quinone disodium salt. The present invention provides crystalline Form A and crystalline Form B of pyrroloquinoline quinone disodium salt, and the methods and uses for the preparation thereof. The X-ray powder diffraction patterns of crystalline Form A and crystalline Form B are as shown by FIG. 1 and FIG. 5, respectively. The crystalline forms of the present invention have low moisture absorption and high stability, as well as excellent use and storage performances.

7 Claims, 18 Drawing Sheets

(56) References Cited

OTHER PUBLICATIONS

Nishigori H. et al., "Preventive effects of pyrroloquinoline quinone on formation of cataract and decline of lenticular and hepatic glutathione of developing chick embryo after glucocorticoid treatment", Life Sci. 45(7):593-8 (1989).

Lili Zhang et al., "The Neuroprotective Effect of Pyrroloquinoline Quinone on Traumatic Brain Injury", Journal of Neurotrauma 29:851-864 (2012).

Hamagishi et al., "New biological properties of pyrroloquinoline quinone and its related compounds: inhibition of chemiluminescence, lipid peroxidation and rat paw edema", J Pharmacol Exp Ther. 255(3):980-5 (1990).

* cited by examiner

CRYSTALLINE FORMS OF PYRROLOQUINOLINE QUINONE DISODIUM SALT

CROSS-REFERENCE TO RELATED APPLICATIONS

This application is a national phase application under 35 U.S.C. 371 of International Application No. PCT/CN2013/083195 filed Sep. 10, 2013,which claims priority to and the benefit of Chinese Application No. 201210452297.6 filed Nov. 9, 2012,both of which applications are hereby incorporated by reference in their entirety.

TECHNICAL FIELD

The invention relates to new crystalline forms of pyrroloquinoline quinone disodium salt and their preparation methods.

BACKGROUND ART

Pyrroloquinoline quinone (PQQ), a compound first discovered in microorganisms, is a prosthetic group of a variety of important enzymes in bacteria. It also exists in the bodies of advanced eukaryotes, and distributes widely in human tissues and organs. As a tasteless and smell-less compound, PQQ has a molecular formula shown as structural formula I:

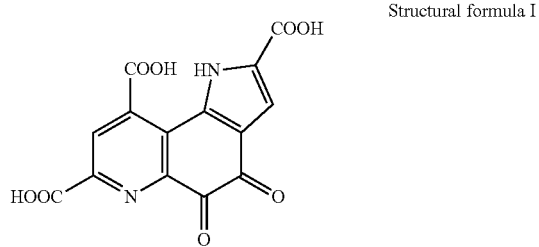 [SMILES: O=C(O)c1cc(C(=O)O)c2c(n1)C(=O)C(=O)c1cc(C(=O)O)[nH]c1-2]

Structural formula I

The research on PQQ in recent years shows that it is a salubrious substance for human. Mice lacking PQQ grow slowly, suffer from poor fertility, and are susceptible to arthritis, indicating that PQQ may be one of the essential vitamins in bodies. As an anti-oxidant, PQQ can protect liver from damage caused by $CCl_4$ or alcohol. Purified PQQ can reduce the formation of glucocorticoid induced cataracta during the development of a chick embryo. PQQ protects neurocytes from the influence of NMDA toxicity, such that cerebral hypoxia-ischemia is prevented and thus severe shock of an animal model is avoided. In addition, PQQ also have functions to prevent and cure myocardial ischemia and myocardial infarction, and is effective in prevention and treatment of artherosclerosis artherosclerosis.

At present, PQQ can be prepared by way of fermentation and chemical synthesis. However, the solid forms of PQQ disodium salt prepared by these methods are unstable and highly hygroscopic. Its wetness varies greatly in the temperature range for ambient storage, and its solid state is undesirable, and thus causing negative influence on the storage and application of PQQ disodium salt.

Mitsubishi Gas Chemical Company, INC. of Japan has filed a patent application for crystal 1 (i.e. crystal E referred to in the present patent application) of PQQ disodium salt (patent literature 1, application number: CN201080031945; application date: Jun. 9, 2010). However, the present inventor has found upon research that this crystal is rather hygroscopic and thus unfavorable for processing and storage.

As such, taking into account the application of PQQ in various fields such as pharmaceuticals, health care, food, etc., there exists an urgent need for PQQ crystals which have high stability, excellent processability and storability in high purity state, and a method for preparing the same.

SUMMARY

One of the main objects of the invention is to provide stable crystalline forms of PQQ disodium salt and their preparation method in consideration of crystallinity, stability, hygroscopicity and/or processability, inter alia. By designing the crystallization conditions for PQQ disodium salt, the present inventor has screened and obtained crystal forms suitable for application in pharmaceuticals, food and health care, etc.

In a first aspect of the invention, there is provided a pyrroloquinoline quinone disodium salt crystalline Form A (i.e., crystal A) which shows diffraction peaks at the following 2θ angles in an X-ray powder diffraction pattern obtained by Cu-K α radiation: 9.6±0.2°, 11.6±0.2°, 14.9±0.2°, 16.0±0.2°, 18.8±0.2°, 19.4±0.2°, 20.4±0.2°, 21.9±0.2°, 22.7±0.2°, 23.2±0.2°, 25.6±0.2°, 33.7±0.2°, 35.0±0.2°, 35.8±0.2°, 36.7±0.2°, 38.0±0.2°, and 38.6±0.2°.

In some embodiments, said crystalline Form A shows diffraction peaks at the following 2θ angles in an X-ray powder diffraction pattern obtained by Cu-K α radiation: 9.2±0.2°, 9.6±0.2°, 11.6±0.2°, 13.5±0.2°, 14.9±0.2°, 16.0±0.2°, 18.2±0.2°, 18.8±0.2°, 19.4±0.2°, 20.4±0.2°, 21.9±0.2°, 22.7±0.2°, 23.2±0.2°, 23.8±0.2°, 25.6±0.2°, 26.4±0.2°, 27.3±0.2°, 28.4±0.2°, 30.7±0.2°, 31.7±0.2°, 32.4±0.2°, 33.7±0.2°, 35.0±0.2°, 35.8±0.2°, 36.7±0.2°, 38.0±0.2°, and 38.6±0.2°.

In some other embodiments, the X-ray powder diffraction pattern of said crystalline Form A obtained by Cu-K α radiation is substantially as shown in FIG. 1.

In a preferred example, said disodium salt crystalline Form A has a hygroscopicity of less than 3% at 25° C. and 65-80% RH.

In another preferred example, the change of hygroscopicity of said disodium salt crystalline Form A is less than 1%, preferably less than 0.6% when humidity varies from 65% RH to 80% RH at 25° C.

In another preferred example, the thermogravimetric analysis curve of said disodium salt crystalline Form A in the range of 30-400° C. is substantially as shown in FIG. 2.

In another preferred example, said disodium salt crystalline Form A is a dihydrate.

In another preferred example, the differential scanning calorimetric analysis graph of said disodium salt crystalline Form A obtained in the range of 50-280° C. at a scanning rate of 10° C./min is substantially as shown in FIG. 3.

In a second aspect of the invention, there is provided a pyrroloquinoline quinone disodium salt crystalline Form B (i.e., crystal B) which shows diffraction peaks at the following 2θ angles in an X-ray powder diffraction pattern obtained by Cu-K α radiation: 8.1±0.2°, 9.0±0.2°, 10.1±0.2°, 13.7±0.2°, 16.4±0.2°, 17.6±0.2°, 18.2±0.2°, 23.9±0.2°, 25.8±0.2°, 27.2±0.2°, 31.0±0.2°, and 39.5±0.2°.

In some embodiments, the peak intensities at the following 2θ angles in the X-ray powder diffraction pattern of said crystalline Form B obtained by Cu-K α radiation are all less than 600.

In a preferred example, the peak intensities at the following 2θ angles in the X-ray powder diffraction pattern of said crystalline Form B obtained by Cu-K α radiation are (2θ/peak intensity): 9.0°/517, 10.1°/366, 16.4°/107, 23.9°/582, 27.2°/511 (although the peak intensities may vary to certain degree due to conditions of experiments and samples, etc, the variation is within the scope predictable to one skilled in the art).

Said disodium salt crystalline Form B has a hygroscopicity of less than or equal to 12.0% at 25° C. and 65-80% RH.

In a preferred example, the change of hygroscopicity of said disodium salt crystalline Form B is less than 1.5%, preferably less than or is 1.0% when humidity varies from 65% RH to 80% RH at 25° C.

In some other embodiments, the X-ray powder diffraction pattern of said crystalline Form B obtained by Cu-K α radiation is substantially as shown in FIG. 5.

In another preferred example, the thermogravimetric analysis curve of said disodium salt crystalline Form B in the range of 30-400° C. is substantially as shown in FIG. 6.

In another preferred example, said disodium salt crystalline Form B is a dihydrate.

In another preferred example, the differential scanning calorimetric analysis graph of said disodium salt crystalline Form B obtained in the range of 50-280° C. at a scanning rate of 10° C./min is substantially as shown in FIG. 7.

In a third aspect of the invention, there is provided a method for preparing said disodium salt crystalline Form A according to the invention, wherein the method is selected from the group consisting of:

(A) suspension crystallization: stirring pyrroloquinoline quinone disodium salt in a solvent to equilibrium at a temperature in the range of 20-60° C. to obtain a suspension, and filtering the suspension to obtain said disodium salt crystalline Form A;

(B) slow volatilization: stirring pyrroloquinoline quinone disodium salt in a solvent, mixing homogeneously to dissolve the salt, and volatizing the solvent at 20-60° C. to obtain said disodium salt crystalline Form A;

(C) anti-solvent precipitation crystallization: dissolving pyrroloquinoline quinone disodium salt in a solvent with high solubility to PQQ at a temperature in the range of 20-60° C., and adding an anti-solvent with low solubility to the resultant system to precipitate said disodium salt crystalline Form A, wherein the solubility of pyrroloquinoline quinone disodium salt in said solvent with high solubility is ≥0.35 g/100 g solvent, and the solubility of pyrroloquinoline quinone disodium salt in said solvent with low solubility is ≤0.15 g/100 g solvent.

In a preferred example, said pyrroloquinoline quinone disodium salt is prepared by chemical synthesis or fermentation.

In another preferred example, said pyrroloquinoline quinone disodium salt comprises or does not comprise crystals.

In another preferred example, said pyrroloquinoline quinone disodium salt may or may not comprise impurities, and has a purity of 98%-100%, preferably 99%-100%.

In another preferred example, in methods (A)-(C), the mass to volume ratio by g/L of said pyrroloquinoline quinone disodium salt to the solvent initially used is 100:1-1:100. In method (A), the mass to volume ratio by g/L of said pyrroloquinoline quinone disodium salt to the solvent initially used is 100:1-1:50, preferably 100:1-1:1. In method (B), the mass to volume ratio by g/L of said pyrroloquinoline quinone disodium salt to the solvent initially used is 50:1-1:100, preferably 10:1-1:100.

In another preferred example, methods (A)-(C) are conducted at room temperature to 55° C., preferably 25-50° C., more preferably room temperature, 25° C. or 50° C.

In another preferred example, the stirring time in methods (A) and (B) is at least 2 hours, preferably 2 hours to 10 days, more preferably 2 hours to 7 days.

In another preferred example, the volatilization time in method (B) is at least 2 hours, preferably 2 hours to 14 days, more preferably 2 hours to 10 days; and the volatilization may be carried out under vacuum.

In another preferred example, the PQQ disodium salt obtained according to any one of methods (A)-(C) has a purity higher than 99.0%, preferably higher than 99.5%, more preferably higher than 99.8% as determined by high performance liquid chromatography.

In some embodiments, the solvents used in methods (A)-(C) are selected respectively from the following groups in which the ratios are based on volume:

Method (A): acetonitrile, methanol, ethanol, water, ethane, heptane, methanol:water, ethanol:water, acetone:water, acetonitrile:water, tetrahydrofuran:water, methanol:hexane, ethanol:hexane, acetonitrile:hexane, tetrahydrofuran:hexane, methanol:methyl tert-butyl ether, ethanol:methyl tert-butyl ether, methanol:toluene, ethanol:toluene, acetonitrile:toluene, methanol:methyl iso-butyl ketone, and toluene:ethane, wherein the volume ratio of the solvents in each mixed solvent is 5:1 to 1:5, preferably 2:1-1:2, more preferably 1:1;

Method (B): methanol:water, ethanol:water, isopropanol:water, acetone:water, acetonitrile:water, and tetrahydrofuran:water, wherein the volume ratio of the solvents in each mixed solvent is 10:1 to 1:10, preferably 5:1-1:5;

Method (C): the solvent with high solubility is water, and the anti-solvent with low solubility is selected from methanol, ethanol, isopropanol, acetone, acetonitrile and tetrahydrofuran.

In a preferred example, when method (A) is conducted at 25° C., the solvent is selected from the following group: acetonitrile, methanol, ethanol, water, methanol:water, ethanol:water, acetone:water, acetonitrile:water, tetrahydrofuran:water, methanol:hexane, ethanol:hexane, acetonitrile:hexane, tetrahydrofuran:hexane, methanol:methyl tert-butyl ether, ethanol:methyl tert-butyl ether, methanol:toluene, ethanol:toluene, acetonitrile:toluene, and methanol:methyl iso-butyl ketone, wherein the volume ratio of the solvents in each mixed solvent is 5:1 to 1:5, preferably 2:1-1:2, more preferably 1:1.

In another preferred example, when method (A) is conducted at 50° C., the solvent is selected from the following group: acetonitrile, methanol, ethanol, ethane, heptane, methanol:water, ethanol:water, acetonitrile:water, tetrahydrofuran:water, methanol:hexane, ethanol:hexane, acetonitrile:hexane, toluene:hexane, methanol:methyl tert-butyl ether, ethanol:methyl tert-butyl ether, methanol:toluene, ethanol:toluene, acetonitrile:toluene, and methanol:methyl iso-butyl ketone, wherein the volume ratio of the solvents in each mixed solvent is 5:1 to 1:5, preferably 2:1-1:2, more preferably 1:1.

In another preferred example, when method (B) is conducted at 25° C., the solvent used is selected from the following group: methanol:water (1:2-1:6), ethanol:water (1:2-1:6), isopropanol:water (1:2), acetone:water (2:9-1:4), acetonitrile:water (2:5-1:4), and tetrahydrofuran:water (2:5-1:4).

In another preferred example, when method (B) is conducted at 50° C., the solvent is selected from the following group: methanol:water (1:6), ethanol:water (1:2), isopropanol:water (1:2), acetone:water (2:9), acetonitrile:water (2:5-1:4), and tetrahydrofuran:water (2:5).

In a fourth aspect of the invention, there is provided a method for preparing said disodium salt crystalline Form B according to the invention, wherein the method is selected from the following group:

(A') suspension crystallization: stirring pyrroloquinoline quinone disodium salt in a solvent to equilibrium at a temperature in the range of 20-60° C. to obtain a suspension, and filtering the suspension to obtain said disodium salt crystalline Form B; or (B') slow volatilization: stirring pyrroloquinoline quinone disodium salt in a solvent, mixing homogeneously to dissolve the salt, and volatizing the solvent at 20-60° C. to obtain said disodium salt crystalline Form B.

In a preferred example, said pyrroloquinoline quinone disodium salt is prepared by chemical synthesis or fermentation.

In another preferred example, said pyrroloquinoline quinone disodium salt comprises or does not comprise crystals.

In another preferred example, said pyrroloquinoline quinone disodium salt may or may not comprise impurities, and has a purity of 98%-100%, preferably 98%-100%.

In another preferred example, in methods (A')-(B'), the mass to volume ratio by g/L of said pyrroloquinoline quinone disodium salt to the solvent initially used is 100:1-1:100. In method (A'), the mass to volume ratio by g/L of said pyrroloquinoline quinone disodium salt to the solvent initially used is 100:1-1:50, preferably 100:1-1:1. In method (B'), the mass to volume ratio by g/L of said pyrroloquinoline quinone disodium salt to the solvent initially used is 50:1-1:100, preferably 10:1-1:100.

In another preferred example, methods (A')-(B') are conducted at room temperature to 55° C., preferably 25-50° C., more preferably room temperature, 25° C. or 50° C.

In another preferred example, the stirring time in method (A') is at least 2 hours, preferably 2 hours to 10 days, more preferably 2 hours to 7 days.

In another preferred example, the volatilization time in method (B') is at least 2 hours, preferably 2 hours to 14 days, more preferably 2 hours to 10 days; and the volatilization may be carried out under vacuum.

In some embodiments, the solvents used in methods (A')-(B') are selected respectively from the following groups in which the ratios are based on volume:

Method (A'): acetone, isopropanol, isopentanol, ethyl acetate, isopropyl acetate, hexane, heptane, methyl tert-butyl ether, methyl isobutyl ketone, dichloromethane, chloroform, tetrahydrofuran, toluene, nitromethane, ethyl ether, methyl ethyl ketone, acetone:ethane, methyl ethyl ketone:ethane, nitromethane:ethane, ethyl acetate:ethane, methyl tert-butyl ether:ethane, toluene:ethane, acetone:methyl tert-butyl ether, methyl ethyl ketone:methyl tert-butyl ether, acetonitrile:methyl tert-butyl ether, tetrahydrofuran:methyl tert-butyl ether, nitromethane:methyl tert-butyl ether, ethyl acetate:methyl tert-butyl ether, acetone:toluene, methyl ethyl ketone:toluene, tetrahydrofuran:toluene, nitromethane:toluene, ethyl acetate:toluene, acetone:methyl isobutyl ketone, methyl ethyl ketone:methyl isobutyl ketone, acetonitrile:methyl isobutyl ketone, tetrahydrofuran:methyl isobutyl ketone, nitromethane:methyl isobutyl ketone, ethyl acetate:methyl isobutyl ketone, methyl tert-butyl ether:methyl isobutyl ketone, toluene: methyl isobutyl ketone, and tetrahydrofuran:ethane, wherein the volume ratio of the solvents in each mixed solvent is 5:1 to 1:5, preferably 2:1-1:2, more preferably 1:1;

Method (B'): isopropanol: water, and tetrahydrofuran: water, wherein the volume ratio of the solvents in each mixed solvent is 10:1 to 1:10, preferably 5:1-1:5, more preferably 4:1-1:4.

In a preferred example, when method (A') is conducted at 25° C., the solvent is selected from the following group: acetone, isopropanol, isopentanol, ethyl acetate, isopropyl acetate, hexane, heptane, methyl tert-butyl ether, methyl isobutyl ketone, dichloromethane, chloroform, tetrahydrofuran, toluene, nitromethane, ethyl ether, methyl ethyl ketone, acetone:ethane, methyl ethyl ketone:ethane, nitromethane:ethane, ethyl acetate:ethane, methyl tert-butyl ether:ethane, toluene:ethane, acetone:methyl tert-butyl ether, methyl ethyl ketone:methyl tert-butyl ether, acetonitrile:methyl tert-butyl ether, tetrahydrofuran:methyl tert-butyl ether, nitromethane:methyl tert-butyl ether, ethyl acetate: methyl tert-butyl ether, acetone:toluene, methyl ethyl ketone:toluene, tetrahydrofuran:toluene, nitromethane:toluene, ethyl acetate:toluene, acetone:methyl isobutyl ketone, methyl ethyl ketone:methyl isobutyl ketone, acetonitrile: methyl isobutyl ketone, tetrahydrofuran:methyl isobutyl ketone, nitromethane:methyl isobutyl ketone, ethyl acetate: methyl isobutyl ketone, methyl tert-butyl ether:methyl isobutyl ketone, and toluene:methyl isobutyl ketone, wherein the volume ratio of the solvents in each mixed solvent is 5:1 to 1:5, preferably 2:1-1:2, more preferably 1:1.

In another preferred example, when method (A') is conducted at 50° C., the solvent is selected from the following group: acetone, isopropanol, isopentanol, ethyl acetate, isopropyl acetate, methyl tert-butyl ether, methyl isobutyl ketone, dichloromethane, chloroform, tetrahydrofuran, toluene, nitromethane, ethyl ether, methyl ethyl ketone, acetone:ethane, methyl ethyl ketone:ethane, tetrahydrofuran:ethane, nitromethane:ethane, ethyl acetate:ethane, methyl tert-butyl ether:ethane, acetone:methyl tert-butyl ether, methyl ethyl ketone:methyl tert-butyl ether, tetrahydrofuran:methyl tert-butyl ether, nitromethane:methyl tert-butyl ether, ethyl acetate:methyl tert-butyl ether, acetone:toluene, methyl ethyl ketone:toluene, tetrahydrofuran:toluene, nitromethane: toluene, ethyl acetate:toluene, acetone:methyl isobutyl ketone, methyl ethyl ketone:methyl isobutyl ketone, acetonitrile:methyl isobutyl ketone, tetrahydrofuran:methyl isobutyl ketone, nitromethane:methyl isobutyl ketone, ethyl acetate:methyl isobutyl ketone, methyl tert-butyl ether:methyl isobutyl ketone, and toluene:methyl isobutyl ketone, wherein the volume ratio of the solvents in each mixed solvent is 5:1 to 1:5, preferably 2:1-1:2, more preferably 1:1.

In another preferred example, when method (B') is conducted at 25° C., the solvent is isopropanol:water (1:4).

In another preferred example, when method (B') is conducted at 50° C., the solvent is tetrahydrofuran:water (1:4).

In another preferred example, the PQQ disodium salt obtained according to either of methods (A')-(B') has a purity high than 98.0%, preferably higher than 99%, more preferably higher than 99.5% as determined by high performance liquid chromatography.

In a fifth aspect of the invention, there is provided a composition or packaged product comprising:

(I) said pyrroloquinoline quinone disodium salt crystalline Form A according to the invention, said pyrroloquinoline quinone disodium salt crystalline Form B according to the invention, said pyrroloquinoline quinone disodium salt crystalline Form A prepared by the method according to the invention and/or said pyrroloquinoline quinone disodium salt crystalline Form B prepared by the method according to the invention; and (II) a medically, physiologically or pharmaceutically acceptable carrier and/or auxiliary.

In some embodiments, said composition or packaged product is selected from the following group: pharmaceutical compositions, functional foods, feedstuffs, additives, microbial inhibitors and preservatives.

In a preferred example, said disodium salt crystal is added at an amount of 0.001 wt % to 99.99 wt %, preferably 0.01 wt % to 99.0 wt %, more preferably 0.1 wt % to 90 wt % by weight of the composition.

In another preferred example, the form of said disodium salt crystal in the composition or packaged product is selected from powder, granule or micropellet, preferably powder.

In another preferred example, said composition or packaged product is used in one or more applications selected from the following group: growth promotion, anti-inflammation, increase of zinc and decrease of lead, prevention and treatment of hepatic diseases, reduction of cataracta development, anti-cancer, promotion of nerve regeneration, prevention and treatment of myocardial infarction and artherosclerosis, dispelling of alcohol effect, prevention/alleviation or treatment of Alzheimer's disease, inhibition of microbial growth, and extension of food storage time.

In another preferred example, said composition or packaged product further comprises one or more additional active substances having activities selected from the following group: growth promotion, anti-inflammation, increase of zinc and decrease of lead, prevention and treatment of hepatic diseases, reduction of cataract development, cancer control, promotion of nerve regeneration, prevention and treatment of myocardial infarction and artherosclerosis, dispelling of alcohol effect, prevention/alleviation or treatment of Alzheimer's disease, inhibition of microbial growth, and extension of food storage time.

In a sixth aspect of the invention, there is provided a use of said pyrroloquinoline quinone disodium salt crystalline Form A according to the invention, said pyrroloquinoline quinone disodium salt crystalline Form B according to the invention, said pyrroloquinoline quinone disodium salt crystalline Form A prepared according to said method of the invention and/or said pyrroloquinoline quinone disodium salt crystalline Form B prepared according to said method of the invention for preparing a pharmaceutical composition or functional food for preventing, alleviating or treating diseases or symptoms by: growth promotion, anti-inflammation, increase of zinc and decrease of lead, prevention and treatment of hepatic diseases, reduction of cataracta development, anti-cancer, promotion of nerve regeneration, prevention and treatment of myocardial infarction and artherosclerosis, dispelling of alcohol effect, Alzheimer's disease, and microbial infection.

In another preferred example, said pharmaceutical composition or functional food comprises one or more additional active substances having activities selected from the following group: growth promotion, anti-inflammation, increase of zinc and decrease of lead, prevention and treatment of hepatic diseases, reduction of cataracta development, anti-cancer, promotion of nerve regeneration, prevention and treatment of myocardial infarction and artherosclerosis, dispelling of alcohol effect, prevention/alleviation or treatment of Alzheimer's disease, inhibition of microbial growth, and extension of food storage time.

Owing to the disclosure herein, other aspects of the invention will be obvious to those skilled in the art. In addition, it is possible for one skilled in the art to make effective combinations of the various features and aspects described herein, and these combinations fall in the claimed protection of the present application as well.

DETAILED DESCRIPTION OF THE INVENTION

Figure 1:
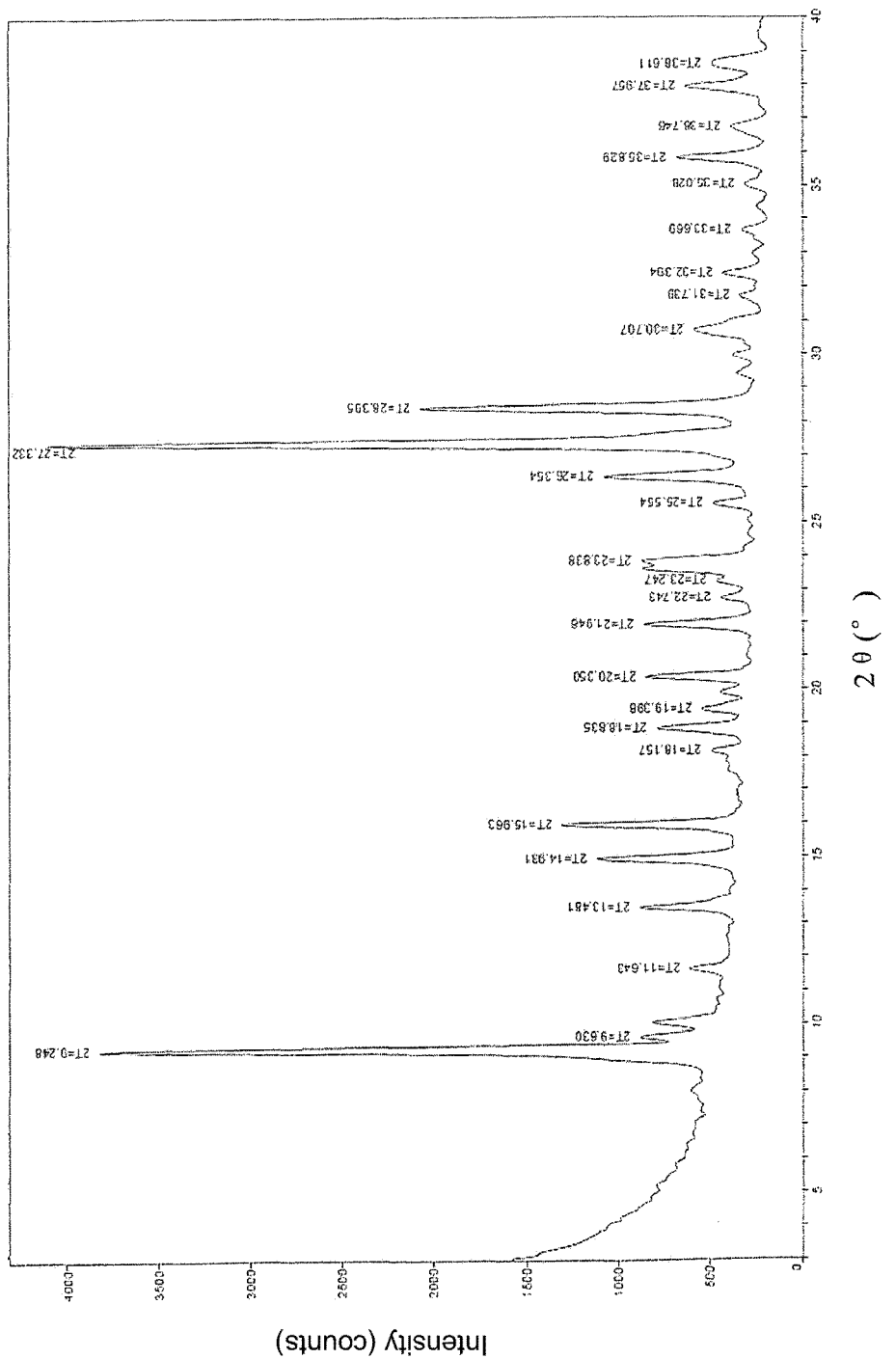
FIG. 1: an X-ray powder diffraction (XRPD) pattern of crystalline Form A obtained in Example 1.

After long-term intensive study, the inventor of the invention has prepared PQQ disodium salt crystalline Forms A and B, and has unexpectedly found that these crystalline forms have high purity, low hygroscopicity, good stability and other superior properties. They are more convenient than the known PQQ disodium salt solid in terms of storage and use, and they are particularly suitable for preparing a composition or packaged product containing PQQ disodium salt. The inventor has fulfilled the invention on this basis.

Preparation of PQQ Disodium Salt Crystals

As used herein, the term "crystal" has the meaning conventionally known in the art, i.e. a solid consisting of crystalline matter inside of which the constituent particles (e.g. atoms, molecules) are periodically arranged in an ordered pattern.

As used herein, the term "pyrroloquinoline quinone" and "PQQ" may be used interchangeably, both referring to the compound having a structural formula shown above as structural formula I. As a starting compound for producing crystalline Form A and crystalline Form B of the invention, the PQQ disodium salt used may be obtained by conventional methods in the art, for example, prepared by fermentation (e.g. patent literature CN 101228963 B) and organic synthesis (J. Am. Chem. Soc., 1981, 103, 5599-5600), etc. The PQQ disodium salt used in the starting material may be crystalline or non-crystalline. In addition, the starting material used may comprise impurities.

Before preparation of the crystals, conventional methods may be employed to measure the solubility of the PQQ disodium salt in different solvents, and subsequently appropriate solvent(s) may be selected to prepare the crystals of the invention. For example, the following method may be used to measure the solubility of the PQQ disodium salt in various solvents:

(1) At 25° C. and 50° C. respectively, about 25 mg PQQ disodium salt is stirred in 1 ml solvent to equilibrium for at least 24 h, and subsequently the solution is filtered, wherein the solvent in the liquid part is volatized under vacuum completely. The approximate solubility of the raw material in the solvent is determined by gravimetric analysis.

Gravimetric analysis: a volume (generally 0.5 mL) of the filtrate is weighed accurately and placed in a vessel which has already been dried and weighed, wherein the weight of the vessel is indicated as $M_{hollow}$. Subsequently, the total weight of the vessel and the filtrate is measured and indicated as $M_0$. Then, the weight of the filtrate is $M_0-M_{hollow}$. After the solvent is volatized completely under vacuum, the total weight is measured accurately again (indicated as $M_1$). Then, the mass of the precipitated solid is $M_1-M_{hollow}$, and the mass of the solvent is $M_0-M_1$. As such, the approximate solubility of the raw material in this solvent is:

$$X(g)=[(M_1-M_{hollow})/(M_0-M_1)]\times 100(g)$$

TABLE 1

Solubility of PQQ disodium salt in various solvents

| Solvent | Solubility @ 25 (g/100 g) | Solubility @ 50 (g/100 g) |
| --- | --- | --- |
| acetone | 0.13 | 0.05 |
| acetonitrile | 0.01 | 0.05 |
| methanol | 0.09 | 0.11 |
| ethanol | 0.08 | 0.11 |
| isopropanol | 0.09 | 0.08 |
| isopentanol | 0.02 | 0.00 |
| ethyl acetate | 0.11 | 0.09 |
| isopropyl acetate | 0.36 | 0.03 |
| hexane | 0.06 | 0.02 |
| heptane | 0.02 | 0.11 |
| methyl tert-butyl ether | 0.05 | 0.03 |
| methyl isobutyl ketone | 0.05 | 0.07 |
| dichloromethane | 0.02 | 0.04 |
| chloroform | 0.02 | 0.03 |
| tetrahydrofuran | 0.15 | 0.24 |
| toluene | 0.02 | 0.05 |
| nitromethane | 0.01 | 0.02 |
| ethyl ether | 0.06 | 0.01 |
| methyl ethyl ketone | 0.16 | 0.06 |
| water | 0.37 | 0.89 |
| methanol:water (1:1) | 0.15 | 0.13 |
| ethanol:water (1:1) | 0.10 | 0.10 |
| acetone:water (1:1) | 0.53 | 1.36 |
| acetonitrile:water (1:1) | 0.22 | 0.14 |
| tetrahydrofuran:water (1:1) | 0.24 | 0.29 |
| acetonitrile:methyl tert-butyl ether (1:1) | 0.10 | 0.04 |
| acetonitrile:methyl tert-butyl ether (1:1) | 0.03 | 0.02 |
| acetonitrile:toluene (1:1) | 0.04 | 0.00 |
| acetonitrile:methyl isobutyl ketone (1.1) | 0.09 | 0.04 |

Preparation of PQQ Disodium Salt Crystalline Form A

PQQ disodium salt crystalline Form A may be prepared by method (A) suspension crystallization, method (B) slow volatilization, or method (C) anti-solvent precipitation crystallization.

Method (A) suspension crystallization, method (B) slow volatilization, and method (C) anti-solvent precipitation crystallization are exemplified as follows. One skilled in the art may adjust the conditions in these methods based on common knowledge.

Method (A): suspension crystallization at 25° C. or 50° C.: PQQ disodium salt is stirred in a solvent to equilibrium for at least 24 h at 25° C. or 50° C., and then filtered to obtain a crystal. Method (B) slow volatilization: PQQ disodium salt is stirred in a solvent, mixed homogeneously and dissolved; and then the solvent is volatized completely at 25° C. or 50° C. to obtain a crystal. Method (C) anti-solvent precipitation crystallization: according to the approximate solubility measured as described above, two solvents having very large difference in solubility at room temperature are used in coordination as a pair. About 5-200 mg PQQ disodium salt is dissolved in 0.5-5 ml of a solvent having very high solubility, and then 4-20 ml of another solvent (anti-solvent) in which PQQ disodium salt is highly insoluble is added, followed by precipitation to obtain a crystal.

Examples of the solvents useful in the operation of method (A) at 25° C. include but are not limited to: acetonitrile, methanol, ethanol, water, methanol:water (1:1), ethanol:water (1:1), acetone:water (1:1), acetonitrile:water (1:1), tetrahydrofuran:water (1:1), methanol:hexane (1:1), ethanol:hexane (1:1), acetonitrile:hexane (1:1), tetrahydrofuran:hexane (1:1), methanol:methyl tert-butyl ether (1:1), ethanol:methyl tert-butyl ether (1:1), methanol:toluene (1:1), ethanol:toluene (1:1), acetonitrile:toluene (1:1), and methanol:methyl iso-butyl ketone (1:1);

Examples of the solvents useful in the operation of method (A) at 50° C. include but are not limited to:

acetonitrile, methanol, ethanol, ethane, heptane, methanol:water (1:1), ethanol:water (1:1), acetonitrile:water (1:1), tetrahydrofuran:water (1:1), methanol:hexane (1:1), ethanol:hexane (1:1), acetonitrile:hexane (1:1), toluene:hexane (1:1), methanol:methyl tert-butyl ether (1:1), ethanol:methyl tert-butyl ether (1:1), methanol:toluene (1:1), ethanol:toluene (1:1), acetonitrile:toluene (1:1), and methanol:methyl iso-butyl ketone (1:1). The mass to volume ratio (g/L) of the raw material to the solvent is 100:1-1:1.

In method (A), when stirring to equilibrium at 25° C. or 50° C. is conducted, it is preferable to stir as desired, and then volatize the solvent completely under vacuum. The stirring time is preferably 2 hours to 7 days.

Examples of the solvents useful in the operation of method (B) at 25° C. include but are not limited to: methanol:water (1:2; 1:6), ethanol:water (1:2; 1:6), isopropanol:water (1:2), acetone:water (2:9; 1:4), acetonitrile:water (2:5; 1:4), and tetrahydrofuran:water (2:5; 1:4). As examples of the solvents useful in slow volatilization at 50° C., the following may be listed: methanol:water (1:6), ethanol:water (1:2), isopropanol:water (1:2), acetone:water (2:9), acetonitrile:water (2:5; 1:4), and tetrahydrofuran:water (2:5). The mass to volume ratio (g/L) of the raw material to the solvent is 10:1-1:100.

With respect to the stirring to equilibrium in method (B), it is preferable to stir as desired, and then volatize the solvent completely at 25° C. or 50° C. The volatilization time is preferably 2 hours to 10 days.

In method (C) anti-solvent precipitation crystallization, the combination of two solvents (solvent/anti-solvent) having large difference in solubility at room temperature includes water/methanol, water/ethanol, water/isopropanol, water/acetone, water/acetonitrile, water/tetrahydrofuran, etc. The mass to volume ratio (g/L) of the raw material to the solvent is 10:1-1:100.

In method (C), the precipitation time after addition of said anti-solvent is set at 2 hours to 2 days.

Extremely pure crystalline Form A may be obtained by method (A), (B) or (C) according to the invention, and its purity may be greater than 99.8% as determined by high performance liquid chromatography.

Preparation of PQQ Disodium Salt Crystalline Form B

PQQ disodium salt crystalline Form B may be prepared by method (A') suspension crystallization, or method (B') slow volatilization. For example, crystalline Form B may be prepared by carrying out method (A') or (B') at 25° C. or 50° C. One skilled in the art may adjust the conditions in these methods based on common knowledge.

Examples of the solvents useful in the operation of method (A') at 25° C. include but are not limited to: acetone, isopropanol, isopentanol, ethyl acetate, isopropyl acetate, hexane, heptane, methyl tert-butyl ether, methyl isobutyl ketone, dichloromethane, chloroform, tetrahydrofuran, toluene, nitromethane, ethyl ether, methyl ethyl ketone, acetone:ethane (1:1), methyl ethyl ketone:ethane (1:1), nitromethane:ethane (1:1), ethyl acetate:ethane (1:1), methyl tert-butyl ether:ethane (1:1), toluene:ethane (1:1), acetone:methyl tert-butyl ether (1:1), methyl ethyl ketone:methyl tert-butyl ether (1:1), acetonitrile:methyl tert-butyl ether (1:1), tetrahydrofuran:methyl tert-butyl ether (1:1), nitromethane:methyl tert-butyl ether (1:1), ethyl acetate:methyl tert-butyl ether (1:1), acetone:toluene (1:1), methyl ethyl ketone:toluene (1:1), tetrahydrofuran:toluene (1:1), nitromethane:toluene (1:1), ethyl acetate:toluene (1:1), acetone:methyl isobutyl ketone (1:1), methyl ethyl ketone:methyl isobutyl ketone (1:1), acetonitrile:methyl isobutyl ketone (1:1), tetrahydrofuran:methyl isobutyl ketone (1:1), nitromethane:methyl isobutyl ketone (1:1), ethyl acetate:methyl isobutyl ketone (1:1), ethyl acetate:methyl isobutyl ketone (1:1), methyl tert-butyl ether:methyl isobutyl ketone (1:1), and toluene:methyl isobutyl ketone (1:1).

Examples of the solvents useful in the operation of method (A') at 50° C. include but are not limited to: acetone, isopropanol, isopentanol, ethyl acetate, isopropyl acetate, methyl tert-butyl ether, methyl isobutyl ketone, dichloromethane, chloroform, tetrahydrofuran, toluene, nitromethane, ethyl ether, methyl ethyl ketone, acetone:ethane (1:1), methyl ethyl ketone:ethane (1:1), tetrahydrofuran:ethane (1:1), nitromethane:ethane (1:1), ethyl acetate:ethane (1:1), methyl tert-butyl ether:ethane (1:1), acetone:methyl tert-butyl ether (1:1), methyl ethyl ketone:methyl tert-butyl ether (1:1), tetrahydrofuran:methyl tert-butyl ether (1:1), nitromethane:methyl tert-butyl ether (1:1), ethyl acetate:methyl tert-butyl ether (1:1), acetone:toluene (1:1), methyl ethyl ketone:toluene (1:1), tetrahydrofuran:toluene (1:1), nitromethane:toluene (1:1), ethyl acetate:toluene (1:1), acetone:methyl isobutyl ketone (1:1), methyl ethyl ketone:methyl isobutyl ketone (1:1), acetonitrile:methyl isobutyl ketone (1:1), tetrahydrofuran:methyl isobutyl ketone (1:1), nitromethane:methyl isobutyl ketone (1:1), ethyl acetate:methyl isobutyl ketone (1:1), methyl tert-butyl ether:methyl isobutyl ketone (1:1), and toluene:methyl isobutyl ketone (1:1). The mass to volume ratio (g/L) of the raw material to the solvent is 100:1-1:1.

In method (A') for preparing crystalline Form B, when stirring to equilibrium at 25° C. or 50° C. is conducted, it is preferable to stir as desired, and then volatize the solvent completely under vacuum. The stirring time is preferably 2 hours to 7 days.

Examples of the solvents useful in the operation of method (B') at 25° C. include but are not limited to isopropanol:water (1:4), etc; and examples of the solvents useful in the operation of method (B') at 50° C. include but are not limited to: tetrahydrofuran:water (1:4). The mass to volume ratio (g/L) of the raw material to the solvent is 10:1-1:100.

With respect to the stirring to equilibrium in method (B'), it is preferable to stir as desired, and then volatize the solvent completely at 25° C. or 50° C. The volatilization time is preferably 2 hours to 10 days.

Identification and Properties of PQQ Disodium Salt Crystalline Forms

After obtaining the PQQ disodium salt crystals, the inventor has further studied their properties using various methods and instruments.

"X-ray powder diffraction", also called "X-ray polycrystalline diffraction (XRPD)", is a common test method used currently to determine crystal structures (i.e. crystal forms). By using an X-ray powder diffractometer, a series of diffraction patterns are produced when X-ray transmits a crystal, wherein different diffraction lines and intensities thereof in the patterns are determined by atomic groups having certain structures, and thus the specific form or structure of the crystal may be determined.

The PQQ disodium salt crystals in the invention have particular crystal forms, and particular characteristic peaks appear in the X-ray diffraction patterns.

PQQ disodium salt crystalline Form A shows diffraction peaks at about the following 2θ angles in an X-ray powder diffraction pattern obtained by Cu-K α radiation: 9.2°, 9.6°, 11.6°, 13.5°, 14.9°, 16.0°, 18.2°, 18.8°, 19.4°, 20.4°, 21.9°, 22.7°, 23.2°, 23.8°, 25.6°, 26.4°, 27.3°, 28.4°, 30.7°, 31.7°, 32.4°, 33.7°, 35.0°, 35.8°, 36.7°, 38.0°, and 38.6° (all ±0.2°).

PQQ disodium salt crystalline Form B shows diffraction peaks at about the following 2θ angles in an X-ray powder diffraction pattern obtained by Cu-K α radiation: 8.1°, 9.0°, 10.1°, 13.7°, 16.4°, 17.6°, 18.2°, 23.9°, 25.8°, 27.2°, 31.0°, and 39.5° (all ±0.2°).

The tests at above diffraction angles 2θ in the X-ray powder diffraction are performed in the following conditions:

Instrument model: Bruker D8 advance
Target: Cu-K α (40 kV, 40 mA)
Distance from sample to detector: 30 cm
Scanning range: 3°-40° (2θ values)
Scanning step: 0.1 s It is to be appreciated that the above peak values can also be observed using a common X-ray powder diffractometer equipped with a monochromator. In addition, measurement error may be included in the crystal forms determined according to the invention as described above. Hence, the peak values are deemed reasonable given that they are within the scope of the measurement error.

The crystals in the invention may also be characterized and studied using differential scanning calorimetric analysis (DSC), thermogravimetric analysis (TG), infrared scanning (IR) and other conventional methods.

As shown by the study, crystals A and B according to the invention may be hydrates (e.g. dihydrates) whose melting points are higher than their decomposition temperatures. They are acceptable so long as they exhibit the peaks measured at the diffraction angles 2θ in the above X-ray powder diffraction.

As compared with the known crystals, crystals A and B according to the invention have remarkably decreased hygroscopicity, such that the crystals according to the invention will not develop easily into undesirable forms such as agglomerates due to absorption of moisture in storage and application, and thus have good stability and processability.

Applications of the Crystals According to the Invention

According to common knowledge in the art, PQQ has medicinal effects in growth promotion, anti-inflammation, increase of zinc and decrease of lead, prevention and treatment of hepatic diseases, reduction of cataracta development, anti-cancer, promotion of nerve regeneration, prevention and treatment of myocardial infarction and artherosclerosis. Additionally, PQQ can also inhibit microbial growth in food, and thus it can extend food storage time.

Hence, crystals A and B according to the invention can be used in combination with "a medically, physiologically or pharmaceutically acceptable carrier" as an effective ingredient in various compositions to be administered to a subject by oral administration, spraying, intranasal administration, or percutaneous administration, etc.

In a composition of the invention, PQQ disodium salt crystals A and/or B as effective ingredients comprise 0.001 wt % to 99.9 wt %, preferably 1 wt % to 95 wt %, more preferably 5 wt % to 90 wt %, still more preferably 10-80 wt % by weight of the composition. The balance is a medically acceptable carrier and other additives, etc.

As used herein, the term "a medically, physiologically or pharmaceutically acceptable carrier" refers to a carrier for health care products or medical formulations, including various excipients and diluents which are not necessary active ingredients per se, and have no toxicity or no undue toxicity after administration. Suitable carriers are known to one skilled in the art. For example, medically acceptable carriers are described detailedly in Remington's Pharmaceutical Sciences (Mack Pub. Co., N.J. 1991).

An acceptable carrier in the composition may comprise liquid, such as water, brine, glycerine and ethanol. In addition, auxiliary materials, such as fillers, disintegrating agents, lubricants, flow aids, effervescing agent, wetting agents or emulsifiers, flavoring agents, pH buffers, etc, may also exist in these carriers. Generally, these substances may be formulated in non-toxic, inert and pharmaceutically acceptable aqueous carrier media, wherein the pH is usually about 5-8, preferably about 6-8. The compositions of the invention may be selected from pharmaceutical compositions, functional foods, feedstuffs, additives, microbial inhibitors and preservatives.

In addition, PQQ crystalline Form A or B may be used alone or in combination with other materials including but not limited to vitamins, amino acids, carotenoids, ω3 fatty acids, ω6 fatty acids, and astaxanthin, etc.

The crystals or compositions of the invention may be made as desired particularly into packaged products, for example, medicine kits, functional food kits, etc, which may comprise PQQ disodium salt crystals according to the invention; optionally, other active substances; directions instructing users or physicians to use the kits; vessels; excipients; etc. One skilled in the art may determine the optional components therein as desired particularly.

The compositions or packaged products of the invention may further comprise one or more additional active substances having activities selected from the following group: growth promotion, anti-inflammation, increase of zinc and decrease of lead, prevention and treatment of hepatic diseases, reduction of cataract development, anti-cancer, promotion of nerve regeneration, prevention and treatment of myocardial infarction and artherosclerosis, dispelling of alcohol effect, prevention/alleviation or treatment of Alzheimer's disease, inhibition of microbial growth, and extension of food storage time. The additional active substances include but are not limited to vitamins, amino acids, carotenoids, ω3 fatty acids, ω6 fatty acids, astaxanthin, etc.

Advantages of the Invention

The main advantages of the invention include:

1. The invention provides two new crystal forms of PQQ disodium salt, i.e. crystalline Form A and crystalline Form B;

2. The crystals A and B according to the invention excel the existing PQQ disodium salt crystals or solids significantly in crystallinity, stability, hygroscopicity and processability, and thus are expected to be used widely in industry, pharmaceuticals, functional foods, and other fields.

EXAMPLES

The invention will be further illustrated with reference to the following specific examples. It is to be understood that these examples are merely intended to demonstrate the invention without limiting the scope thereof. One skilled in the art can make appropriate modifications and changes to the invention, which modifications and changes are all included in the scope of the invention.

The experimental methods in the following examples for which no specific conditions are indicated may be carried out using conventional procedures in the art, for example, with reference to Crystalline Pharmaceuticals (Lv Yang, Du Guanhua, ed., People's Medical Publishing House, 2009), or under those conditions suggested by the manufacturers. Tests may also be provided by commercial companies. All the reagents in the following examples are commercially available.

Unless otherwise indicated, all percentages and parts are based on weight. Unless otherwise defined, all special and scientific terms used herein have the same meaning as those familiar to those skilled in the art. In addition, any method and material similar or equivalent to those cited herein may be used in the method of the invention. The preferred implementing methods and materials described herein are intended to be exemplary only.

Reference Example

Preparation of PQQ Disodium Salt

PQQ disodium salt was obtained by the following operations:

Based on the chemical synthesis process reported by Corey, et al, in a literature published in 1981 (J. Am. Chem. Soc., 1981, 103, 5599-5600), the synthetic process routes and conditions were modified by optimization, and PQQ disodium salt was obtained after nine-step reactions.

Compared with the literature of Corey, the optimization and modification in the method of the invention were reflected in the following aspects: 1) noble metal platinum, which was used as a catalyst in the catalytic hydrogenation in the literature, was replaced with palladium; 2) methyl 2-methylacetylacetate, which was used as a coupling agent in the diazotization coupling reaction in the literature, was replaced with ethyl 2-methylacetylacetate; and, 3) the ester hydrolyzation in the literature, wherein the ester reacted with an orthoformate first to produce a monoketal which was then hydrolyzed to obtain the final product under alkaline conditions, was changed into direct hydrolyzation under alkaline conditions followed by pH adjustment to obtain the product.

The specific synthetic procedure was as follows:

(1) Formylation reaction: the amino group in the raw material, 2-methoxyl-5-nitroaniline, was protected by formylation under the action of formic acid and acetic anhydride to obtain N-(2-methoxyl-5-nitrophenyl) formamide;

(2) Catalytic hydrogenation reaction: with ethanol as the solvent and palladium/carbon as the catalyst, the nitro group on the aromatic ring of the compound in which the amino group was protected by formylation was reduced into amino group to obtain N-(5-amino-2-methoxylphenyl)formamide;

(3) Diazotization coupling reaction: under the action of sodium nitrite, the amino group was diazotized to form diazonium fluoroborate which coupled with ethyl 2-methylacetylacetate directly to obtain ethyl 2-{[(3-formamido-4-methoxyl)aryl]hydrazono}-propionate;

(4) Reaction for forming pyrrole ring: a pyrrole ring was formed in the product obtained in the preceding step under the action of formic acid to obtain ethyl 6-formamido-5-methoxyl-1H-indole-2-carboxylates;

(5) Hydrolyzation reaction of formamide: the amido bond in the formamido group protected in the first step was deprotected under acidic conditions to free the amino group to obtain ethyl 6-amino-5-methoxyl-1H-indole-2-carboxylates;

(6) Cyclization reaction: the product with the amino group freed in the preceding step and dimethyl 2-oxo-glutaconate were subjected to cyclization reaction to obtain 9-hydroxyl-5-methoxyl-6,7,8,9-tetrahydro-1H-pyrrolo[2,3-f]quinoline-2,7,9-tricarboxylic acid-2-ethyl ester-7,9-dimethyl ester;

(7) Formation of quinoline ring: a quinoline ring was formed with the product obtained in the preceding step in the presence of cupric acetate under acidic conditions to obtain 5-methoxyl-1H-pyrrolo[2,3-f]quinoline-2,7,9-tricarboxylic acid-2-ethyl ester-7,9-dimethyl ester;

(8) Oxidation reaction: a quinone ring was formed with the product obtained in the preceding step under the action of an oxidant to obtain 4,5-dioxo-4,5-dihydro-1H-pyrrolo[2,3-f]quinoline-2,7,9-tricarboxylic acid-2-ethyl ester-7,9-dimethyl ester;

(9) Ester hydrolyzation reaction: the three ester groups in the PQQ ester were hydrolyzed under alkaline conditions; after hydrolyzation, pH of the solution was adjusted to 3.0 using 6 mol/L hydrochloric acid; and after holding for 3 hours, the solid, i.e. PQQ disodium salt, was separated.

The raw PQQ disodium salt was crystalline Form C.

The purity of the PQQ disodium salt was higher than 99.0% as measured by high performance liquid chromatography under the conditions indicated as follows:

Instrument model: UlTiMate3000, Dionex, USA

Chromatographic column: YMC-C18 250×4.6 mm I.D.

Mobile phase: acetonitrile: 100 mM potassium dihydrophosphate=12:88, pH adjusted to 2.0 using phosphoric acid Detection wavelength: 249 nm Column temperature: 35° C.

Flowing rate: 1.0 ml/min

Injection volume: 10 μl

Embodiment Example 1

Preparation of PQQ Disodium Salt Crystalline Form A by Suspension Crystallization and Study on the Properties of the Resultant Crystal Ten milligram PQQ disodium salt prepared according to the method described in the above Reference Example (purity ≥98; PQQ disodium salt available from Sigma Co. may also be used, catalog number: 80198-10MG-F) was stirred in 1 mL acetonitrile to equilibrium for 5 days at 25° C. or 50° C. Subsequently, the solution was filtered, and the solid part was dried in air for 10 minutes to obtain PQQ disodium salt crystalline Form A.

Figure 2:
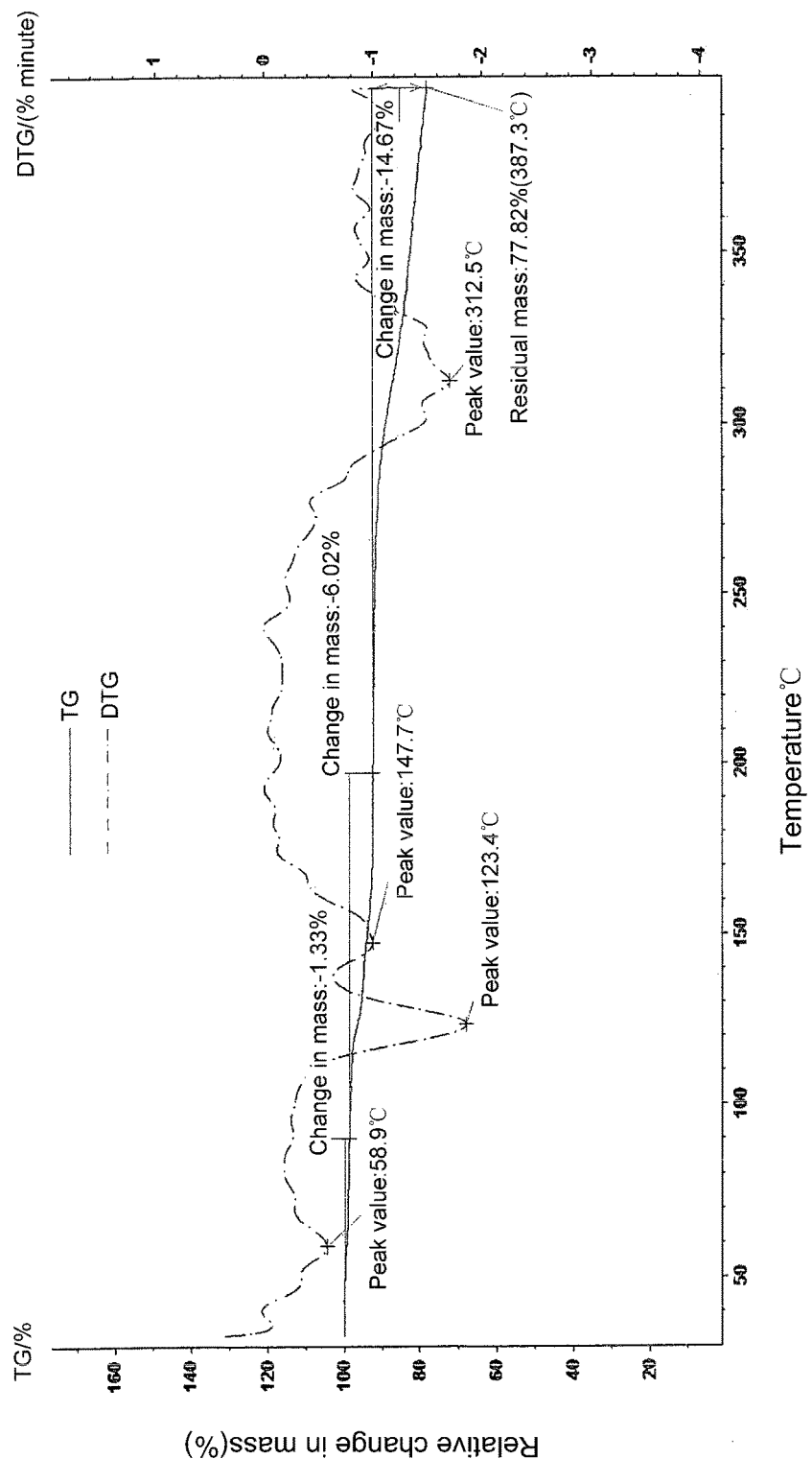
FIG. 2: a thermogravimetric analysis (TG) graph of crystalline Form A obtained in Example 1.
Figure 3:
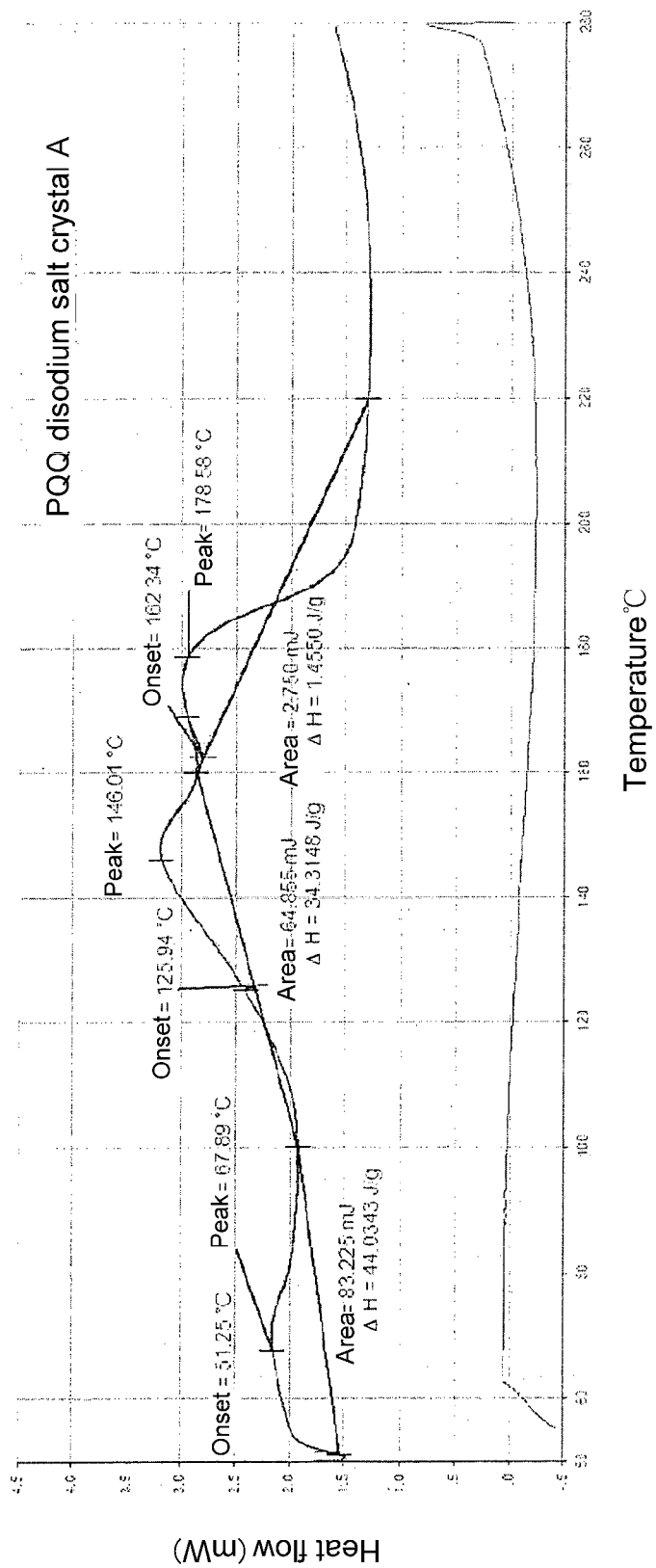
FIG. 3: a differential scanning calorimetric analysis (DSC) graph of crystalline Form A obtained in Example 1.
Figure 4:
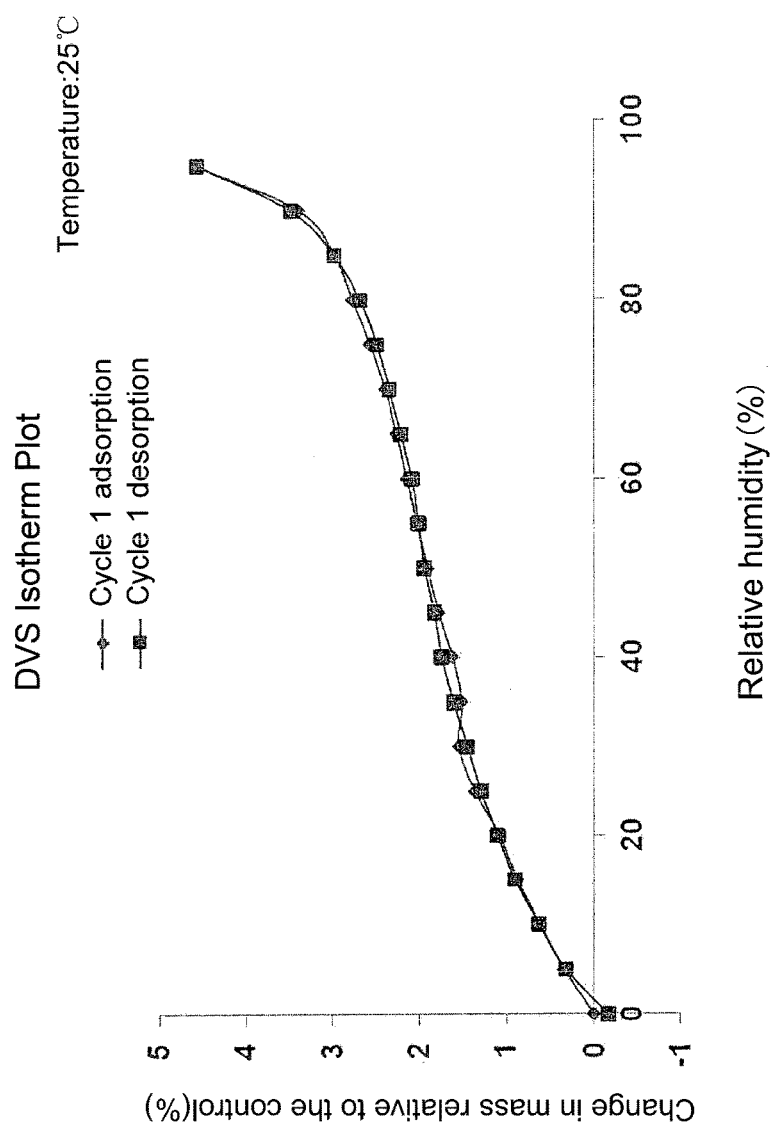
FIG. 4: a hygroscopic analysis (DVS) graph of crystalline Form A obtained in Example 1.

The resultant PQQ disodium salt crystalline Form A was subjected to X-ray powder diffraction analysis (XRPD, FIG. 1), thermogravimetric analysis (TG, FIG. 2), differential scanning calorimetric analysis (DSC, FIG. 3) and hygroscopic analysis (DVS, FIG. 4).

1. X-Ray Powder Diffraction Pattern

The X-ray powder diffraction pattern of the resultant crystal was obtained under the following conditions. The results are shown in FIG. 1. The peaks obtained by X-ray powder diffraction using Cu-K α radiation appear at the 2θ angles of about: 9.2°, 9.6°, 11.6°, 13.5°, 14.9°, 16.0°, 18.2°, 18.8°, 19.4°, 20.4°, 21.9°, 22.7°, 23.2°, 23.8°, 25.6°, 26.4°, 27.3°, 28.4°, 30.7°, 31.7°, 32.4°, 33.7°, 35.0°, 35.8°, 36.7°, 38.0°, and 38.6° (all ±0.2°).

Instrument model: Bruker D8 advance
Target: Cu-K α (40 kV, 40 mA)
Distance from sample to detector: 30 cm
Scanning range: 3°-40° (2θ values)
Scanning step: 0.1 s
The solid obtained was crystalline.

2. Thermogravimetric Analysis

As indicated by TG (FIG. 2), crystalline Form A exhibits weight loss of 1.33% and 6.02% at two positions in the range of 30-200° C. (the theoretical weight loss of a water molecule is 4.6%). It is possibly a hydrate. The peak temperature of decomposition is 312.5° C.

Instrument model: Netzsch TG 209F3
Temperature range: 30-400° C.
Scanning rate: 10 K/min
Purging gas: 25 mL/min
Protection gas: 15 mL/min 3. Differential Scanning Calorimetric Analysis In the corresponding DSC (FIG. 3), endothermic peaks appear in this temperature range (30-200° C.), indicating that this crystalline Form Contains water. In addition, no melting phenomenon occurs in the rising temperature range, indicating that the melting point of this crystal may be above its decomposition temperature.

Instrument model: Perkin Elmer DSC 8500
Temperature range: 50-280° C.
Scanning rate: 10° C./min
$N_2$ flowing rate: 50 ml/min 4. Hygroscopic Analysis As indicated by DVS (FIG. 4), crystalline Form A absorbs 1.6% of moisture at 40% RH, 2.3% at 65% RH, and 2.8% at 80% RH. In a conventional storage environment of 40-80 RH, the variation of hygroscopicity is less than 2%, showing that the crystal is only slightly hygroscopic.

Instrument model: SMS DVS Intrinsic, 0-95% RH,
Temperature: 25° C.

Embodiment Example 2

Preparation of PQQ Disodium Salt Crystalline Form A by Slow Volatilization and Study on the Properties of the Resultant Crystal Two portions of 3 mg PQQ disodium salt (prepared in the Reference Example) were provided, and mixed with a solvent comprising 160 μL absolute ethanol+560 μL water and a solvent comprising 160 μL absolute ethanol+320 μL water, respectively. They were dissolved, and then volatized slowly to dry at 25° C. and 50° C., respectively. After the solvent was volatized completely, drying under reduced pressure was carried out to obtain PQQ disodium salt crystalline Form A.

Under the conditions described in Embodiment Example 1, the X-ray powder diffraction pattern of the resultant crystal was obtained, and thermogravimetric analysis, differential scanning calorimetric analysis and hygroscopic analysis were carried out. The results were the same as those in Embodiment Example 1.

Embodiment Example 3

Preparation of PQQ Disodium Salt Crystalline Form A by Anti-Solvent Precipitation Crystallization and Study on the Properties of the Resultant Crystal Ten milligram PQQ disodium salt (prepared in the Reference Example) was dissolved in 2 mL water and stirred to equilibrium. Subsequently, it was placed into a brown glass bottle containing 6 mL absolute ethanol, and the precipitate settled out after 12 hours. The solid filtered out was dried under pressure to obtain PQQ disodium salt crystalline Form A.

Under the conditions described in Embodiment Example 1, the X-ray powder diffraction pattern of the resultant crystal was obtained, and thermogravimetric analysis, differential scanning calorimetric analysis and hygroscopic analysis were carried out. The results were the same as those in Embodiment Example 1.

Embodiment Example 4

Preparation of PQQ Disodium Salt Crystalline Form B by Suspension Crystallization and Study on the Properties of the Resultant Crystal Ten milligram PQQ disodium salt (prepared in the Reference Example) was stirred in 1 mL ethyl acetate to equilibrium for 5 days at 25° C. or 50° C. Subsequently, the solution was filtered, and the solid part was dried under reduced pressure to obtain PQQ disodium salt crystalline Form B.

Figure 6:
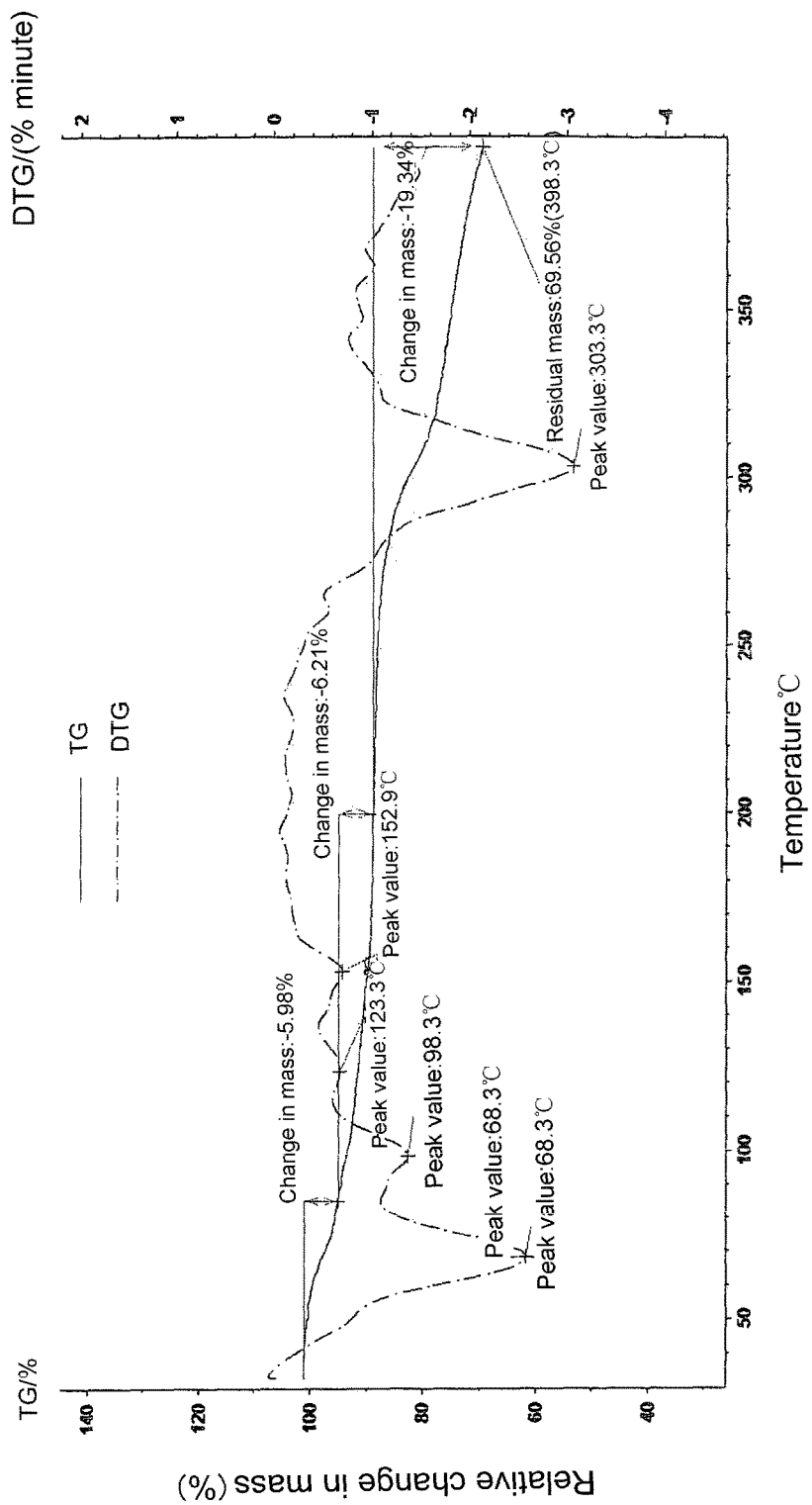
FIG. 6: a thermogravimetric analysis (TG) graph of crystalline Form B obtained in Example 4.
Figure 7:
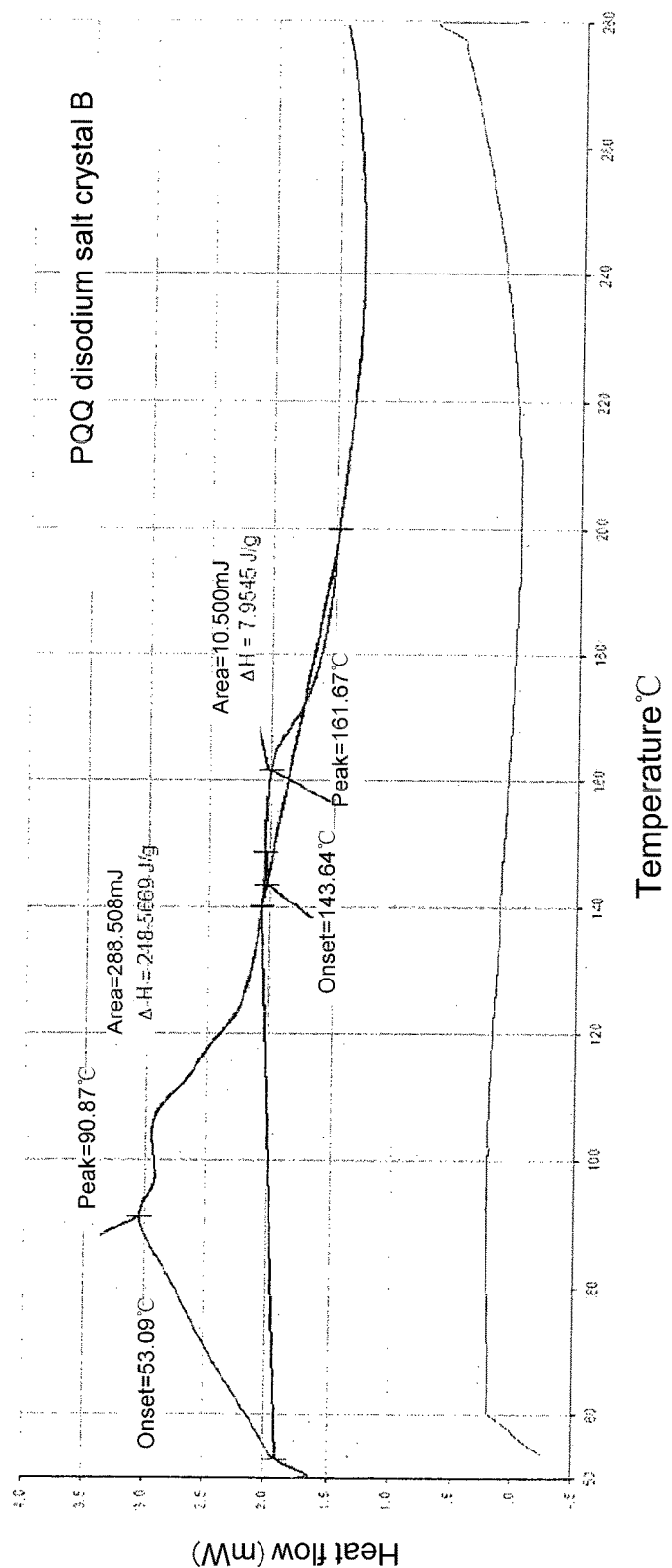
FIG. 7: a differential scanning calorimetric analysis (DSC) graph of crystalline Form B obtained in Example 4.
Figure 8:
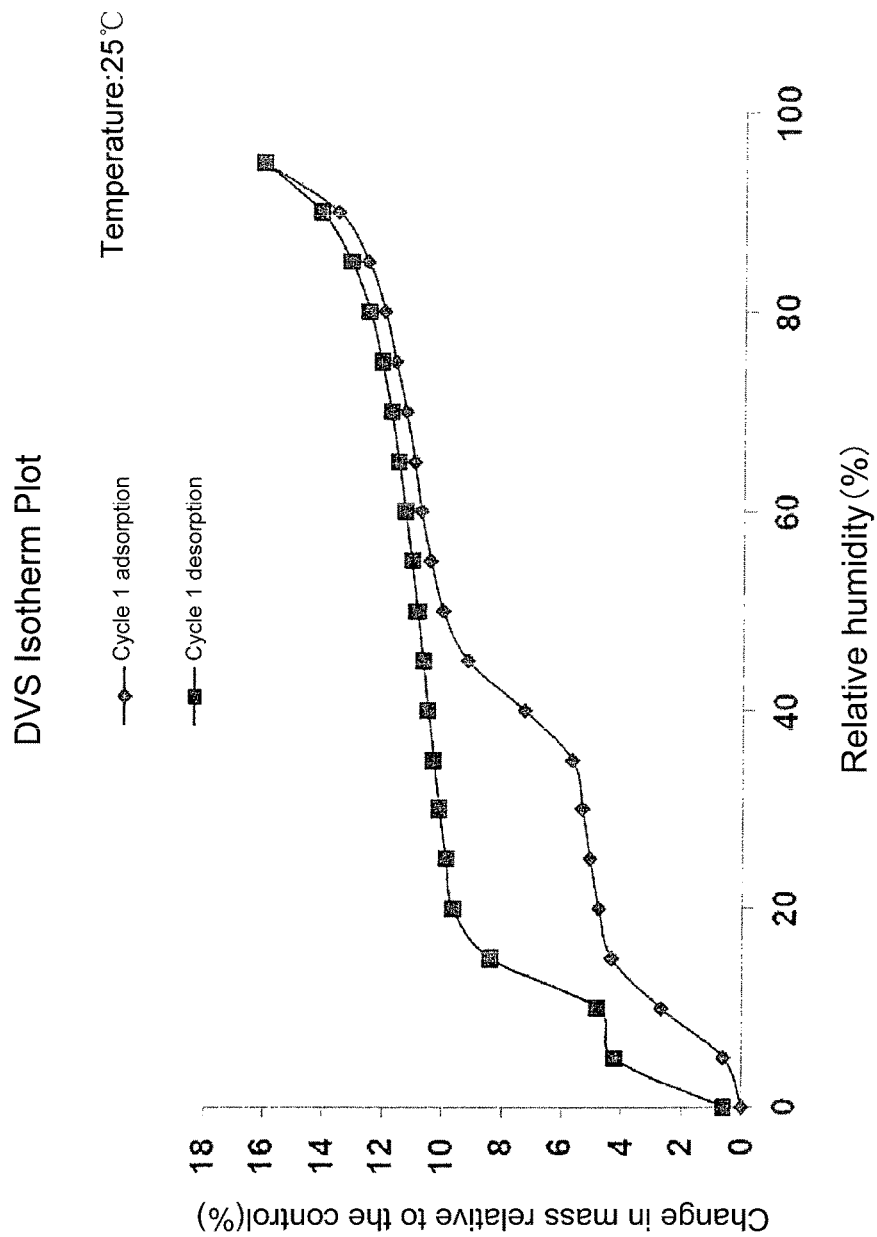
FIG. 8: a hygroscopic analysis (DVS) graph of crystalline Form B obtained in Example 4.

Under the conditions indicated in Embodiment Example 1, the resultant PQQ disodium salt crystalline Form B was subjected to X-ray powder diffraction analysis (XRPD, FIG. 5), thermogravimetric analysis (TG, FIG. 6), differential scanning calorimetric analysis (DSC, FIG. 7) and hygroscopic analysis (DVS, FIG. 8):

1. X-Ray Powder Diffraction Pattern

Figure 5:
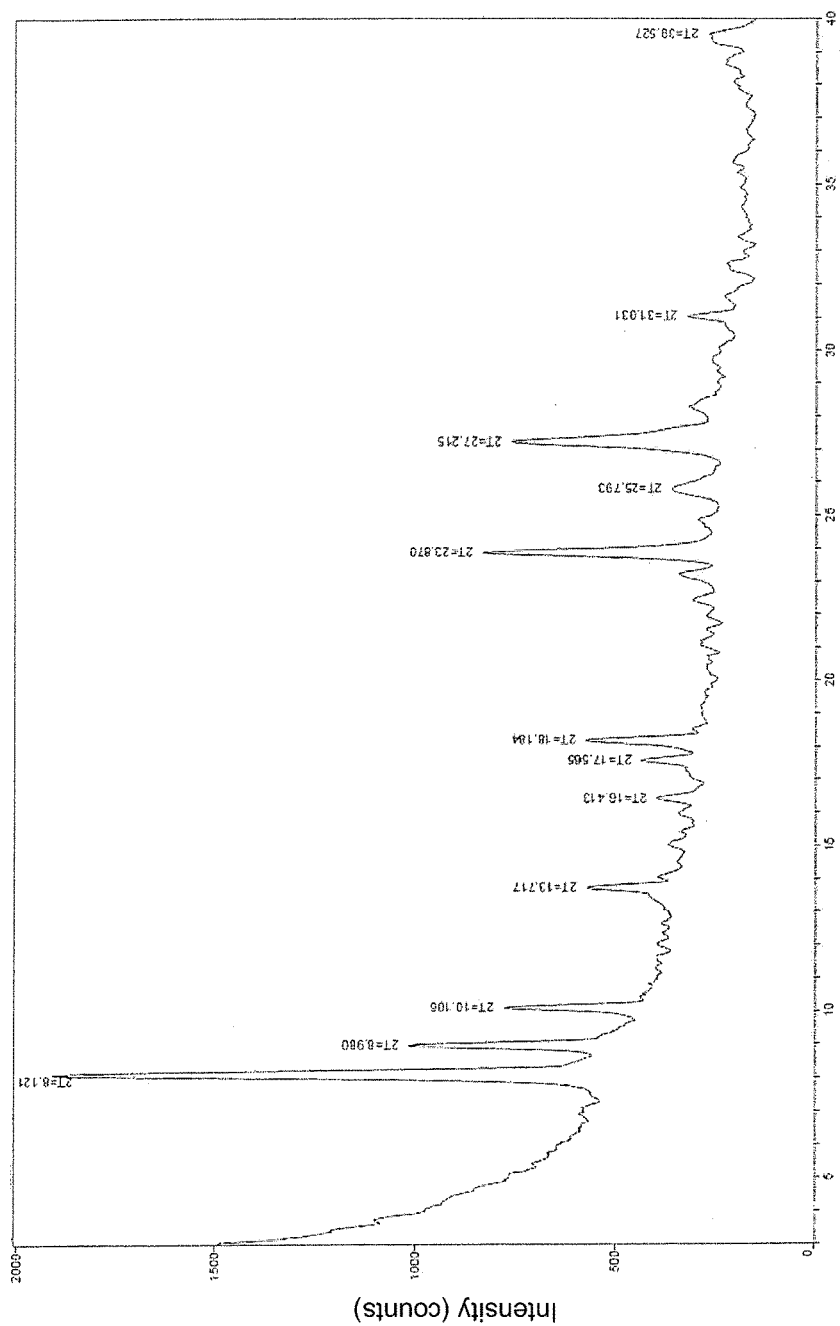
FIG. 5: an X-ray powder diffraction (XRPD) pattern of crystalline Form B obtained in Example 4.

The X-ray powder diffraction pattern of the resultant crystalline Form B was obtained. The results are shown in FIG. 5. The peaks obtained by X-ray powder diffraction using Cu-K α radiation appear at the 2θ angles of 8.1°, 9.0°, 10.1°, 13.7°, 16.4°, 17.6°, 18.2°, 23.9°, 25.8°, 27.2°, 31.0°, and 39.5° (all ±0.2°).

2. Thermogravimetric Analysis

As indicated by TG (FIG. 6), crystalline Form B exhibits two weight loss zones of 5.98% and 6.21% in the range of 30-200° C. (the theoretical weight loss of a water molecule is 4.6%, and the theoretical weight loss of an ethyl acetate molecule is 19.1%). It is possibly a hydrate. The peak temperature of decomposition is 303.3° C.

3. Differential Scanning Calorimetric Analysis

In the corresponding DSC (FIG. 7), endothermic peaks appear in this temperature range, indicating that this crystalline Form Contains water. In addition, no melting phenomenon occurs in the rising temperature range, indicating that the melting point of crystalline Form B may be above its decomposition temperature.

4. Hygroscopic Analysis

As indicated by DVS (FIG. 8), crystalline Form B absorbs 7.3% of moisture at 40% RH, 11.0% at 65% RH, and 12.0% at 80% RH. In the range of 20-40 RH, a monohydrate is formed; in the range of greater than 50 RH, dihydrate is formed; and when the humidity increases further, a polyhydrate may be formed.

Embodiment Example 5

Preparation of PQQ Disodium Salt Crystalline Form B by Slow Volatilization and Study on the Properties of the Resultant Crystal Two portions of 3 mg PQQ disodium salt were provided, one of which was mixed homogeneously with a solvent comprising 160 μL isopropanol+960 μL water and was dissolved, followed by volatilization to dry at 25° C.; and, the other of which was mixed homogeneously with a solvent comprising 160 μL tetrahydrofuran+640 μL water and was dissolved, followed by volatilization at 50° C. After the solvent was volatized completely, drying under reduced pressure was carried out to obtain PQQ disodium salt crystalline Form B.

Under the conditions described in Embodiment Example 1, the X-ray powder diffraction pattern of the resultant crystal was obtained, and thermogravimetric analysis, differential scanning calorimetric analysis and hygroscopic analysis were carried out. The results were the same as those in Embodiment Example 4.

Comparative Embodiment Example 1

Preparation of PQQ Disodium Salt Crystalline Form C and Study on the Properties of the Resultant Crystal For the method of obtaining PQQ disodium salt crystalline Form C, see Reference Example for details.

Figure 10:
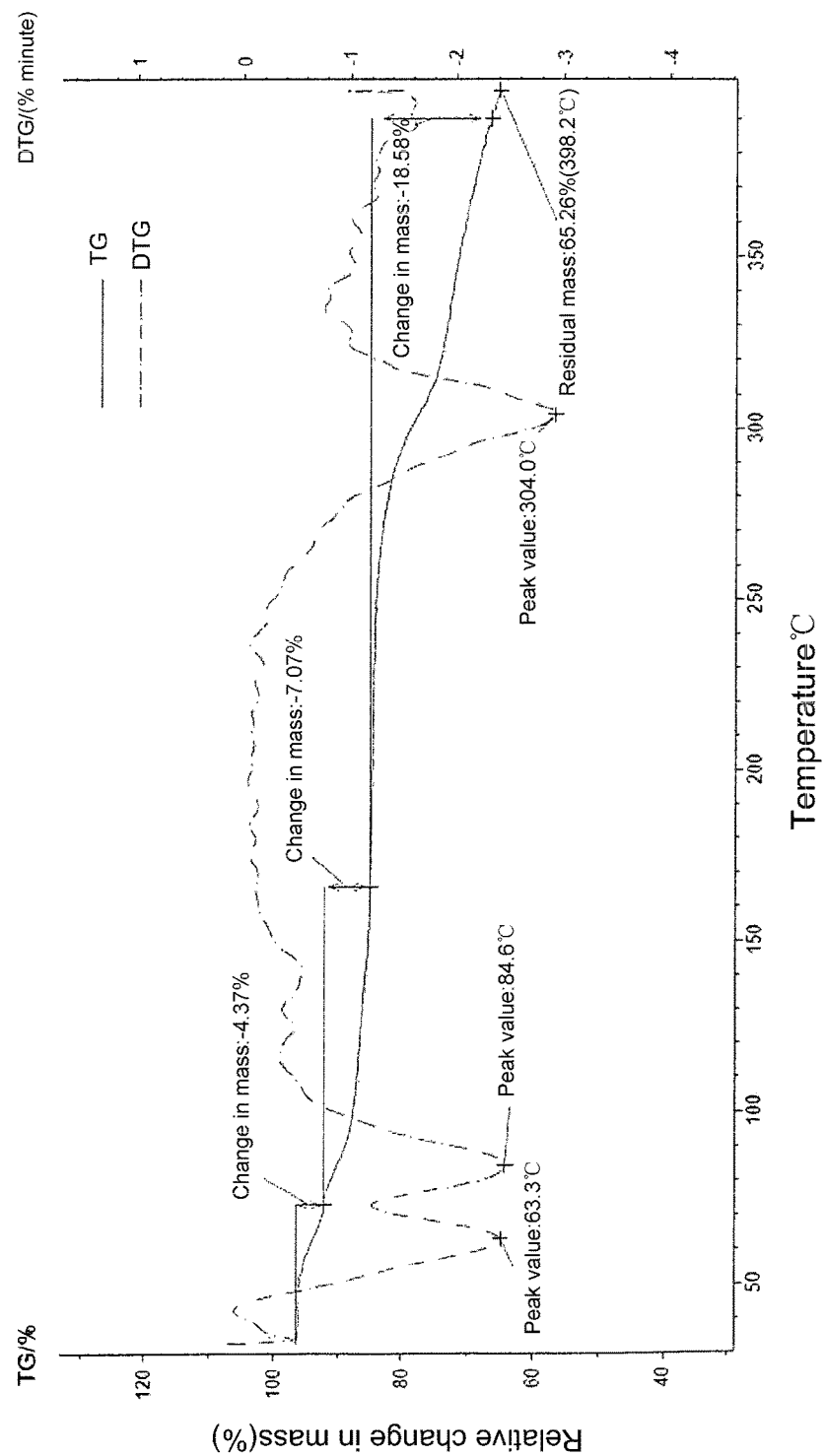
FIG. 10: a thermogravimetric analysis (TG) graph of crystalline Form C obtained in Comparative Example 1.
Figure 11:
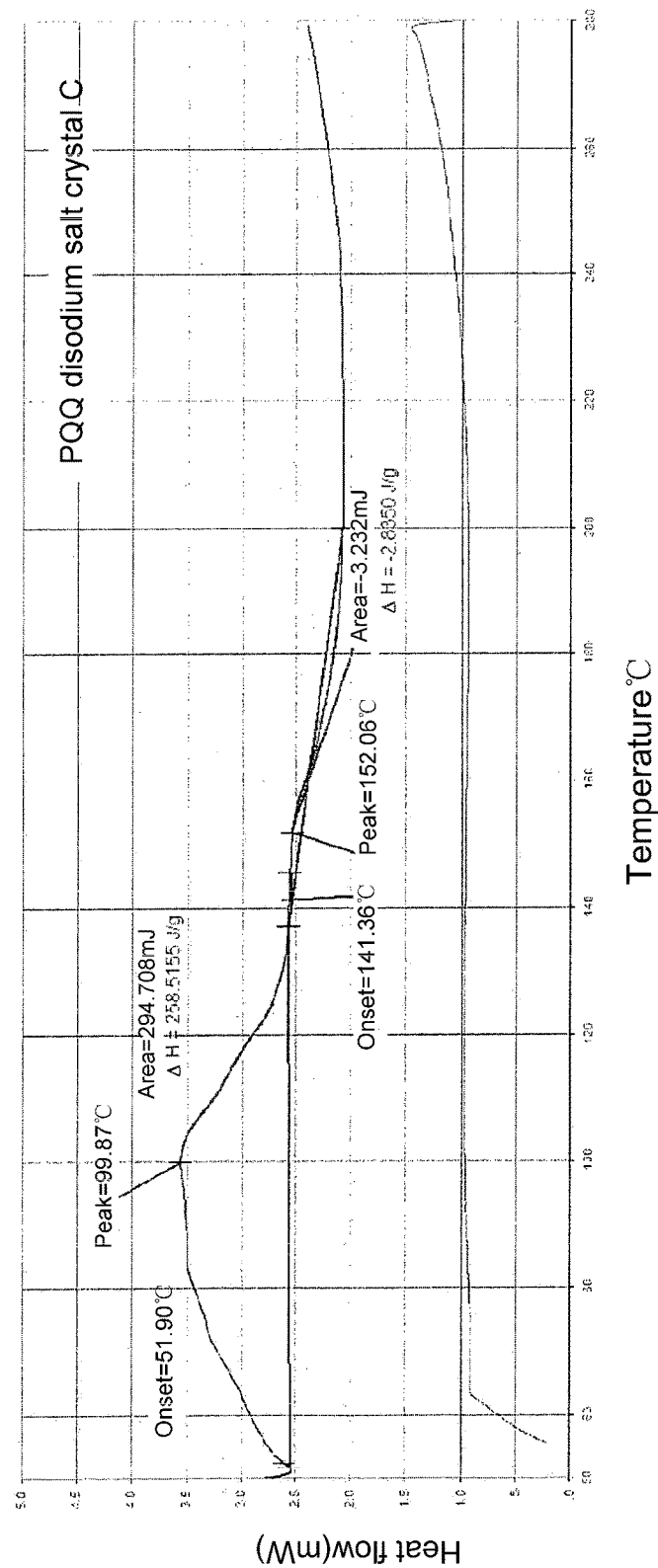
FIG. 11: a differential scanning calorimetric analysis (DSC) graph of crystalline Form C obtained in Comparative Example 1.
Figure 12:
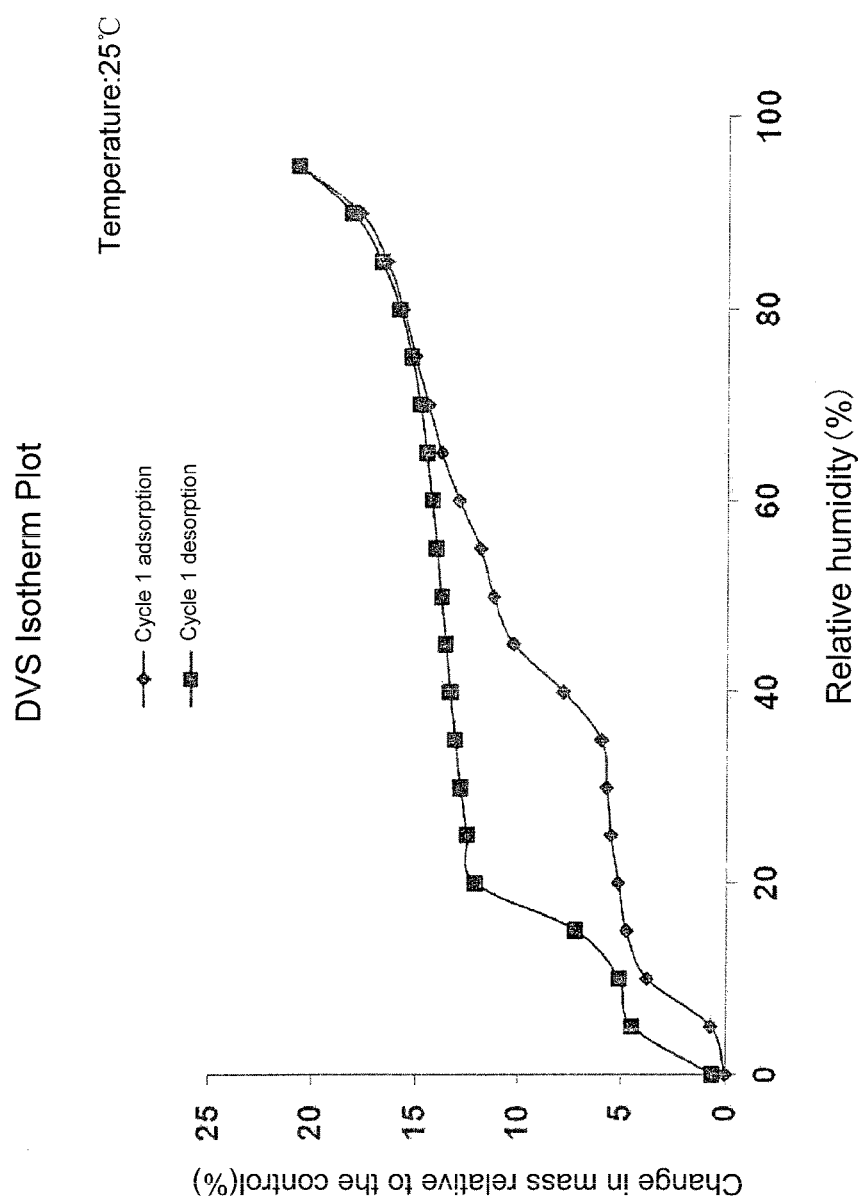
FIG. 12: a hygroscopic analysis (DVS) graph of crystalline Form C obtained in Comparative Example 1.
Figure 13A:
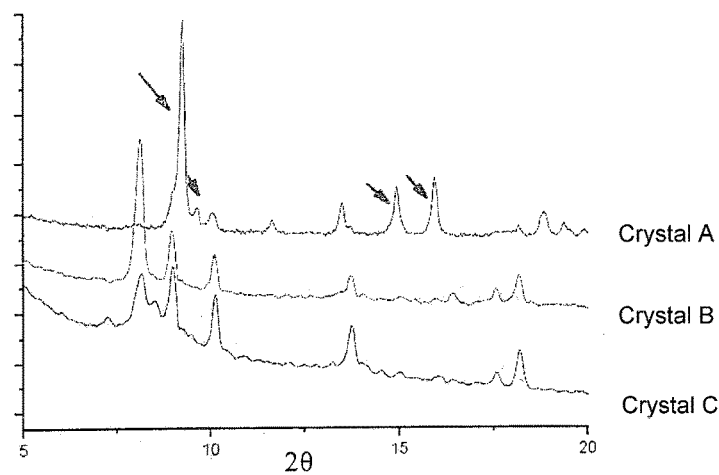
FIG. 13A: an overlay of XRPD patterns of crystals A, B and C for comparison.
Figure 13B:
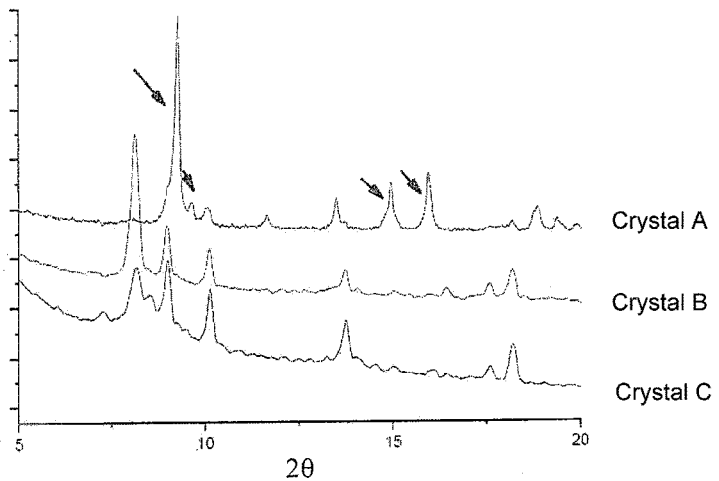
FIG. 13B: an overlay of enlarged XRPD patterns of crystals A, B and C for comparison 1.
Figure 13C:
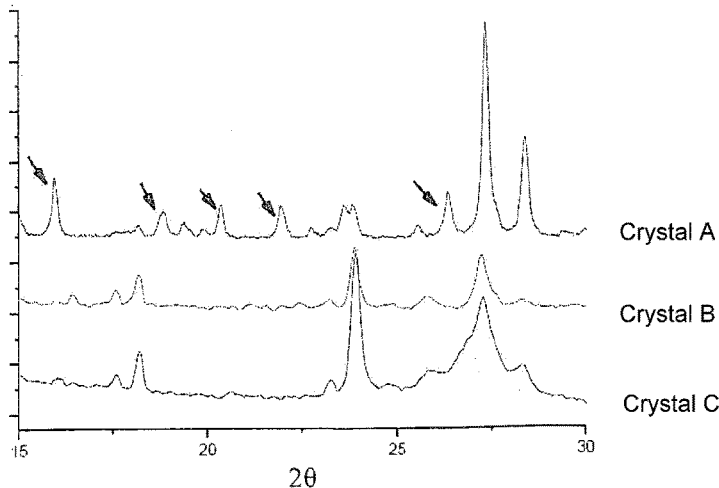
FIG. 13C: an overlay of enlarged XRPD patterns of crystals A, B and C for comparison 2.
Figure 14:
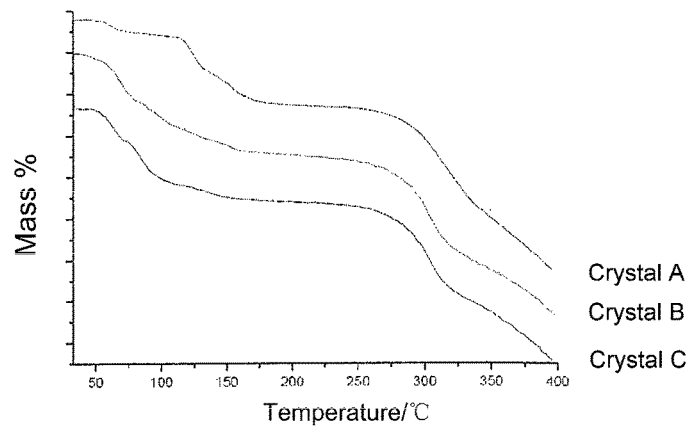
FIG. 14: an overlay of TG graphs of crystals A, B and C for comparison.
Figure 15:
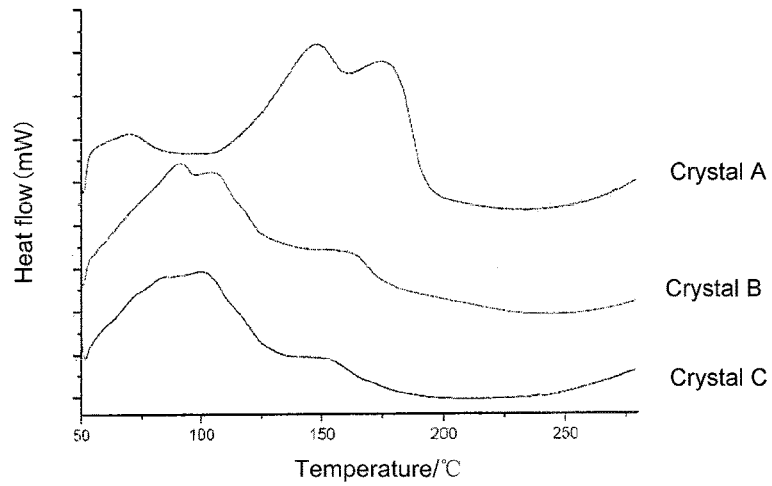
FIG. 15: an overlay of DSC graphs of crystals A, B and C for comparison.
Figure 16:
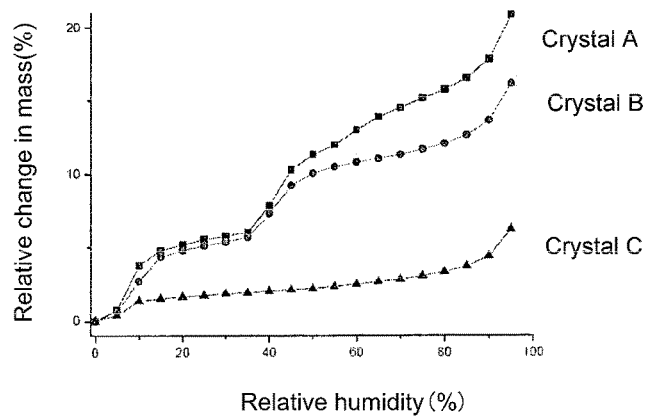
FIG. 16: an overlay of DVS graphs of crystals A, B and C for comparison.
Figure 17A:
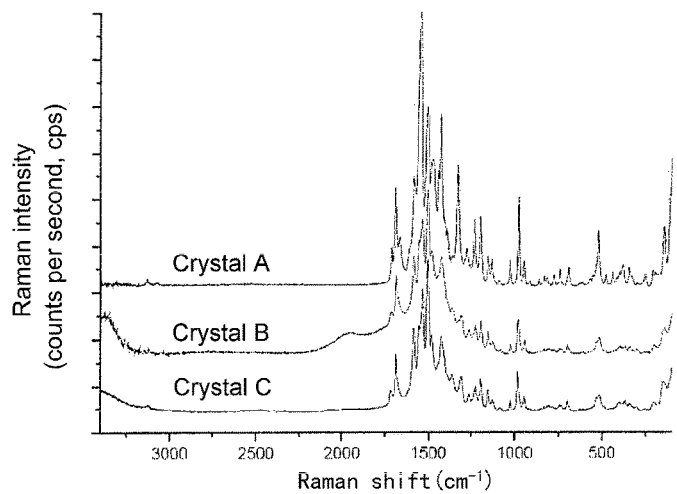
FIG. 17A: an overlay of Raman spectra of crystals A, B and C for comparison.
Figure 17B:
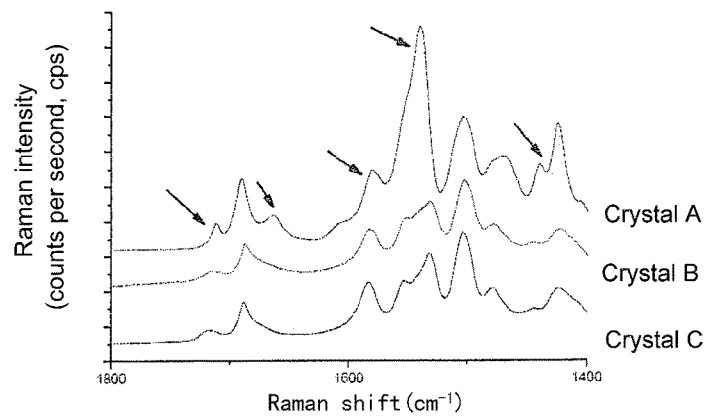
FIG. 17B: an overlay of enlarged Raman spectra of crystals A, B and C for comparison 1.
Figure 17C:
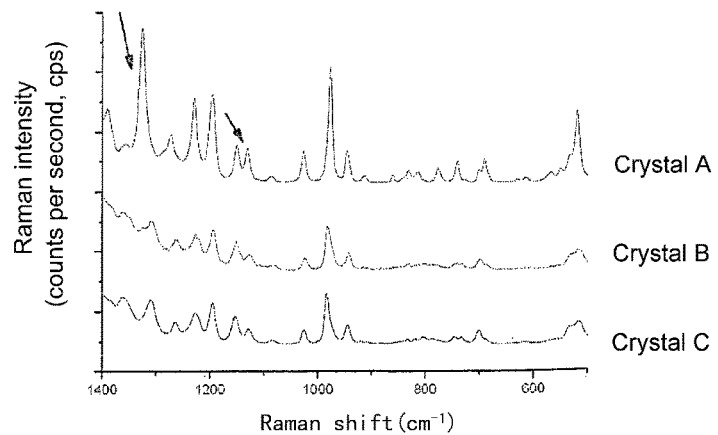
FIG. 17C: an overlay of enlarged Raman spectra of crystals A, B and C for comparison 2.
Figure 18A:
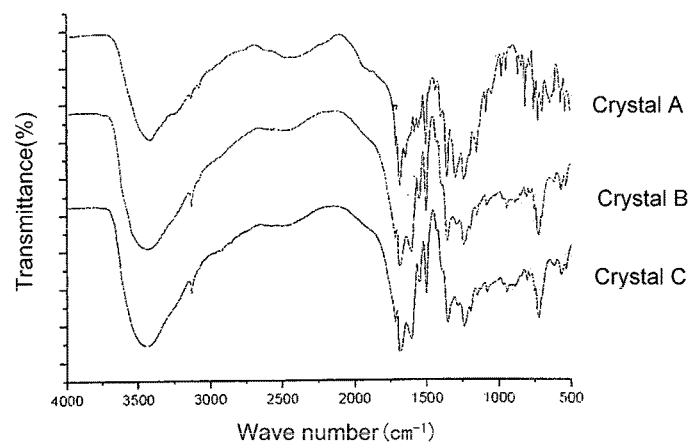
FIG. 18A: an overlay of Infrared (IR) spectra of crystals A, B and C for comparison.
Figure 18B:
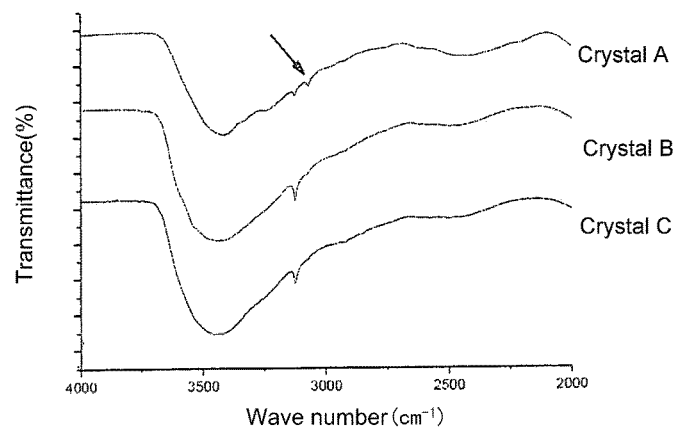
FIG. 18B: an overlay of enlarged IR spectra of crystals A, B and C for comparison 1.
Figure 18C:
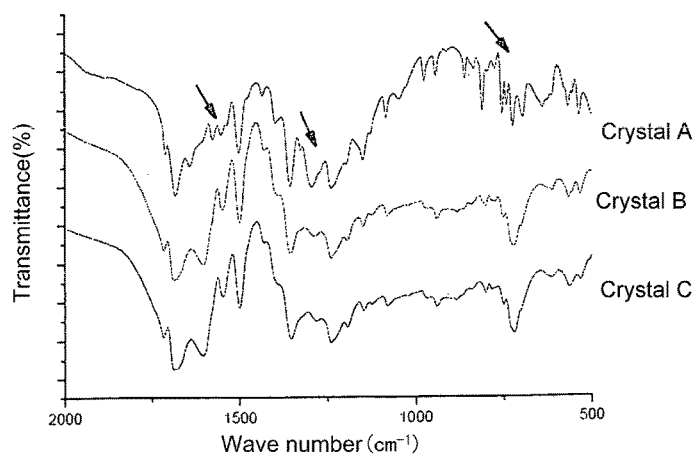
FIG. 18C: an overlay of enlarged IR spectra of crystals A, B and C for comparison 2.

Under the conditions indicated in Embodiment Example 1, the resultant PQQ disodium salt crystalline Form C was subjected to X-ray powder diffraction analysis (XRPD, FIG. 9), thermogravimetric analysis (TG, FIG. 10), differential scanning calorimetric analysis (DSC, FIG. 11) and hygroscopic analysis (DVS, FIG. 12):

1. X-Ray Powder Diffraction Pattern

Figure 9:
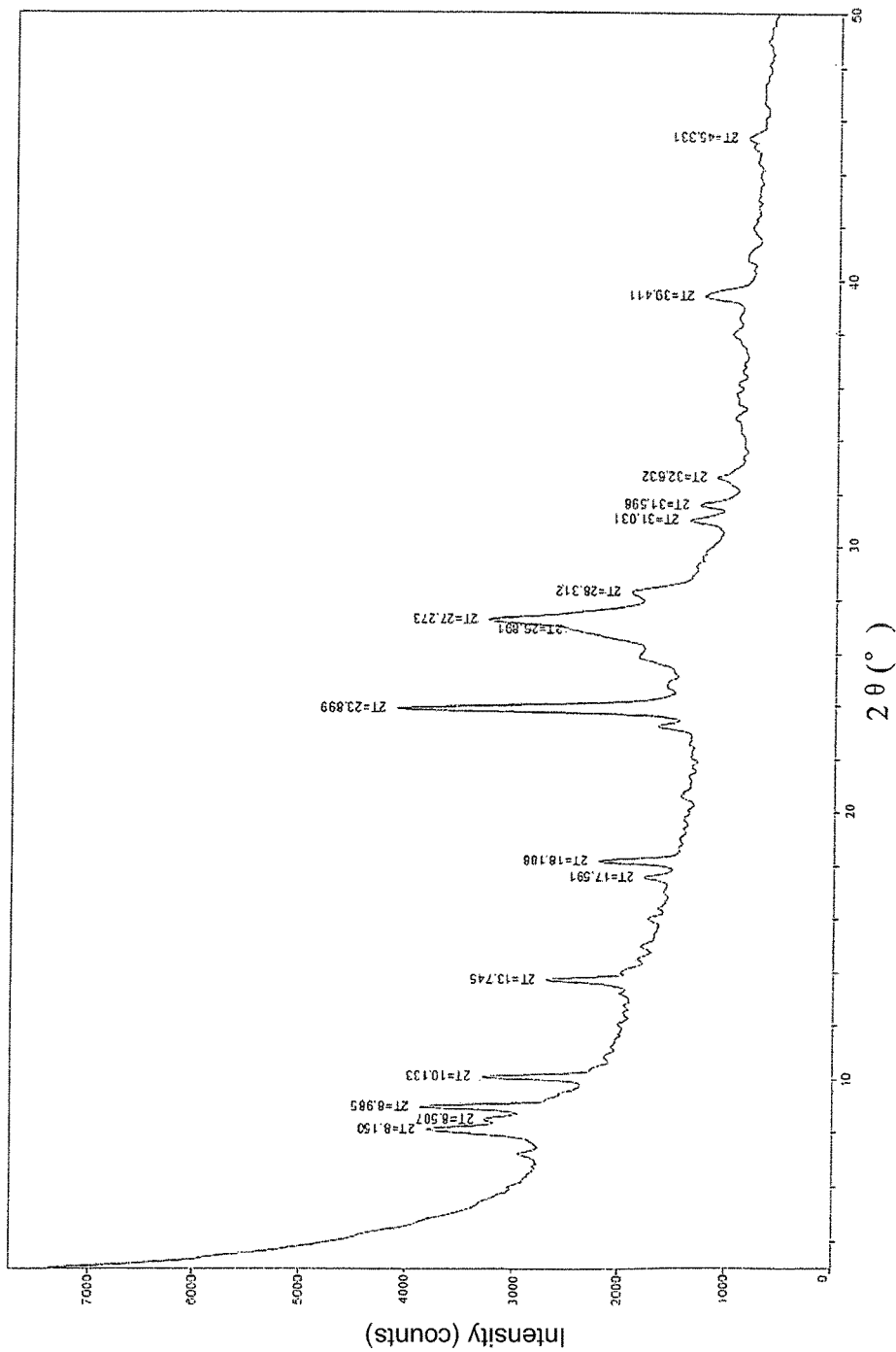
FIG. 9: an X-ray powder diffraction (XRPD) pattern of crystalline Form C (i.e., crystal C) obtained in Comparative Example 1.

The results of the X-ray powder diffraction pattern of crystalline Form C are shown in FIG. 9. The peaks obtained by X-ray powder diffraction using Cu-K α radiation appear at the 2θ angles of 8.2°, 8.6°, 9.0°, 10.1°, 13.7°, 17.6°, 18.2°, 23.9°, 26.9°, 27.3°, 28.3°, 31.0°, 31.6°, 32.6°, 39.4°, and 45.3° (±0.2°).

2. Thermogravimetric Analysis

As indicated by TG (FIG. 10), obvious weight loss at the beginning of the test was observed, which shows the existence of surface water in a relatively large amount. Additionally, crystalline Form C exhibits two weight loss zones of 4.37% and 7.06% in the range of 30-180° C. (the theoretical weight loss of a water molecule is 4.6%). It is possibly a hydrate.

3. Differential Scanning Calorimetric Analysis

In the corresponding DSC (FIG. 11), endothermic peaks appear in this temperature range, indicating that this crystalline Form Contains water.

4. Hygroscopic Analysis

As indicated by DVS (FIG. 12), crystalline Form C is highly hygroscopic. In the conventional range of humidity for storage, its wetness varies significantly, specifically from 5% to 15%. It contains 7.8% of moisture at 40% RH. It absorbs 13.8% of moisture at 65% RH, and 15.7% at 80% RH. As a preliminary inference, in the range of 20-40 RH, a monohydrate is formed; in the range of greater than 50 RH, dihydrate is formed; and when the humidity increases further, a polyhydrate may be formed.

Comparative Embodiment Example 2

Conversion of Single Crystal Data to X-Ray Powder Diffraction Results

Figure 19:
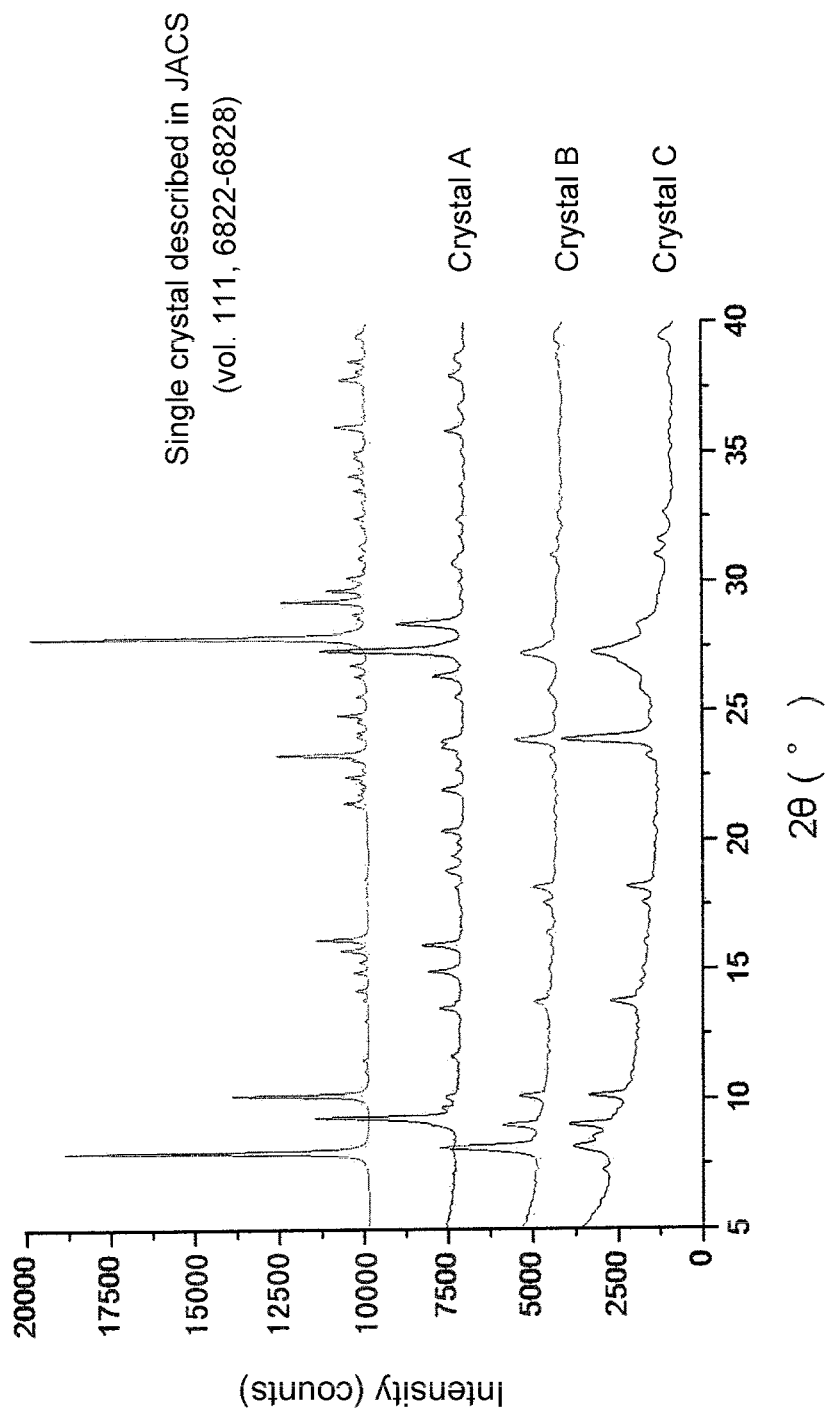
FIG. 19: an overlay of XRPD patterns of crystals A, B, crystalline Form C and crystal D (a PQQ sodium salt crystalline Form appearing as a single crystal in JACS, *Journal of the American Chemical Society*, August, 1989, vol. 111, no. 17, 6822-6828) for comparison.

The single crystal data for X-ray crystalline structural identification reported in a non-patent literature (JACS, vol. 111, 6822-6828) were used to model the X-ray powder diffraction peaks generated by this crystal (crystal D). The results obtained using Origin drawing software are shown in FIG. 19. As indicated by the results, the positions of the peaks are different from those of the crystals of the present invention (see Table 2 for details).

Comparative Embodiment Example 3

The Crystal Described in Patent Literature 1

The X-ray powder diffraction results of crystal 1 described in literature 1 (referred to as crystal E in the present invention) were compared with those of crystals A and B according to the present invention. As indicated by the results, the positions of the peaks are different from those of the crystals of the present invention (see Table 2 for details).

Comparative Example

Comparison Between PQQ Disodium Salt Crystals A, B and Crystals C, D, E

The three crystals (i.e. crystals A, B and C) obtained in the examples were compared by ways of XRPD, TG, DSC, DVS, Raman spectrum and infrared spectrum (IR), wherein the test methods of XRPD, TG, DSC and DVS were described in Embodiment Example 1.

Raman spectrum
Instrument model: Thermo DXR Raman Microscope
Exposure time (second): 2.0
Laser: 780 nm
Laser power: 50 mW
Laser: 25 μm slit
IR
Instrument model: Nicolet FTIR 6700
Resolution: 4.000
Sample collection: 2.0
Optical velocity: 0.6329
Aperture: 100.00
Detector: DTGS KBr
Beamsplitter: KBr The results of comparison between crystalline Form A obtained in Embodiment Example 1, crystalline Form B obtained in Embodiment Example 4, crystalline Form C obtained in Comparative Embodiment Example 1, crystal D obtained in Comparative Embodiment Example 2 and crystal E described in Comparative Embodiment Example 3 (patent literature 1, application number: CN201080031945) are summarized in Table 2, Table 3 and overlays of the graphs (FIGS. 13-18).

TABLE 2

Crystal form Designation

| PQQ disodium salt crystalline Form A | | PQQ disodium salt crystalline Form B | | PQQ disodium salt crystalline Form C | | Crystal D | Crystal E |
|---|---|---|---|---|---|---|---|
| Embodiment Examples 1, 2, 3 | | Embodiment Examples 4, 5 | | Comparative Embodiment Example 1 | | Comparative Embodiment Example 2 | Patent literature 1 |
| 2θ | Peak intensity | 2θ | Peak intensity | 2θ | Peak intensity | 2θ | 2θ |
| | | | | 7.2° | 166 | | |
| | | 8.1° | 1404 | 8.2° | 1028 | 7.9° | |
| | | | | 8.6° | 584 | | |
| 9.2° | 3520 | 9.0° | 517 | 9.0° | 1125 | | 9.1° |
| 9.6° | 406 | | | | | | |
| | | 10.1° | 366 | 10.1° | 1083 | 10.1° | 10.3° |
| 11.6° | 208 | | | | | | |
| 13.5° | 550 | 13.7° | 238 | 13.7° | 913 | | 13.8° |
| | | | | | | 14.2° | |
| 14.9° | 798 | | | | | 14.9° | |
| | | | | | | 15.7° | |
| 16.0° | 1021 | 16.4° | 107 | | | 16.2° | |
| | | 17.6° | 159 | 17.6° | 284 | | 17.7° |
| 18.2° | 155 | 18.2° | 291 | 18.2° | 728 | | 18.3° |
| 18.8° | 449 | | | | | | |
| 19.4° | 210 | | | | | | |
| 20.4° | 573 | | | 20.7 | 121 | | |
| | | | | | | 21.4° | |
| 21.9° | 595 | | | | | 21.8° | |
| 22.7° | 132 | | | | | 22.4° | |
| | | | | | | 23.1° | |
| 23.2° | 166 | | | 23.2 | 204 | 23.3° | |
| 23.8° | 585 | 23.9° | 582 | 23.9° | 2701 | 24.1° | 24.0° |
| | | | | | | 24.6° | |
| | | | | | | 24.8° | |
| 25.6° | 192 | 25.8° | 116 | 25.8 | 162 | | |
| 26.4° | 753 | | | 26.9° | 639 | 26.3° | |
| | | | | | | 26.8° | |
| 27.3° | 3924 | 27.2° | 511 | 27.3° | 1466 | | 27.4° |
| | | | | | | 27.8° | |
| 28.4° | 1798 | | | 28.3° | 266 | | |
| | | | | | | 29.2° | |
| | | | | | | 29.7° | |
| | | | | | | 30.1° | |
| 30.7° | 340 | | | | | | |
| | | 31.0° | 136 | 31.0° | 351 | 31.3° | 31.2° |
| 31.7° | 101 | | | 31.6° | 271 | | |
| 32.4° | 207 | | | 32.6° | 241 | 32.4° | |
| 33.7° | 129 | | | | | 33.5° | |
| | | | | | | 34.1° | |
| | | | | | | 34.4° | |
| | | | | | | 34.8° | |
| 35.0° | 97 | | | | | 35.0° | |
| 35.8° | 488 | | | | | 36.0° | |
| 36.7° | 181 | | | | | | |
| | | | | | | 37.8° | |
| 38.0° | 441 | | | | | 38.1° | |
| 38.6° | 277 | | | | | 38.5° | |
| | | 39.5° | 98 | 39.4° | 388 | 39.4° | 39.5° |
| | | | | 45.3° | 156 | | |

(characteristic peaks relative to crystalline Form C are indicated in bold)

TABLE 3

| | Crystal form | Solvent content (%) | Hygroscopicity | Crystal form stability |
|---|---|---|---|---|
| Embodiment Example 1 | crystalline Form A | 7.4 | 65% RH, moisture absorption of 2.3% 80% RH, moisture absorption of 2.8% | Stable |
| Embodiment Example 4 | crystalline Form B | 12.2 | 65% RH, moisture absorption of 11.0% 80% RH, moisture absorption of 12.0% | Stable |

TABLE 3-continued

| Crystal form | Solvent content (%) | Hygroscopicity | Crystal form stability |
|---|---|---|---|
| Comparative Embodiment Example 1 crystalline Form C | 11.4% | 65% RH, moisture absorption of 13.8% 80% RH, moisture absorption of 15.7% | Converted into crystalline Form B |

3. Analysis on the Overlays of Graphs Characterizing Various Crystal Solids

As indicated by the overlay of the XRPD graphs (FIGS. 13A-C), crystalline Form A is apparently different from crystals B and C at 9.2°, 9.6°, 14.9°, 16.0°, etc., and the peak intensity of crystalline Form B is apparently different from that of crystalline Form C at 9.0°, 10.1°, 16.4°, 23.9°, and 27.2°.

As indicated by the overlay of TG graphs (FIG. 14), crystals A, B and C all exhibit weight loss due to solvent.

As indicated by the overlay of DSC graphs (FIG. 15), crystals A, B and C all show endothermic peaks, and the melting points of crystals A, B and C are above their decomposition temperatures.

As indicated by the overlay of DVS graphs (FIG. 16), the hygroscopicity of the three crystal forms is different, wherein crystalline Form A, absorbing 2.8% of moisture at 80% RH, shows the smallest hygroscopicity; crystalline Form B, absorbing 12.0% of moisture at 80% RH, shows the medium hygroscopicity; and crystalline Form C, absorbing 15.7% of moisture at 80% RH, shows the largest hygroscopicity.

As indicated by the overlay of Raman spectra (FIGS. 17A-C), crystalline Form A is different from crystals B and C at 1579.70 cm$^{-1}$, 1539.20 cm$^{-1}$, 1327.07 cm$^{-1}$, etc.

As indicated by the overlay of infrared spectra (IR) (FIGS. 18A-C), crystalline Form A is different from crystals B and C at 3072.05 cm$^{-1}$, 1577.49 cm$^{-1}$, 1295.93 cm$^{-1}$, etc.

Comparative Example 2.

Figure 20:
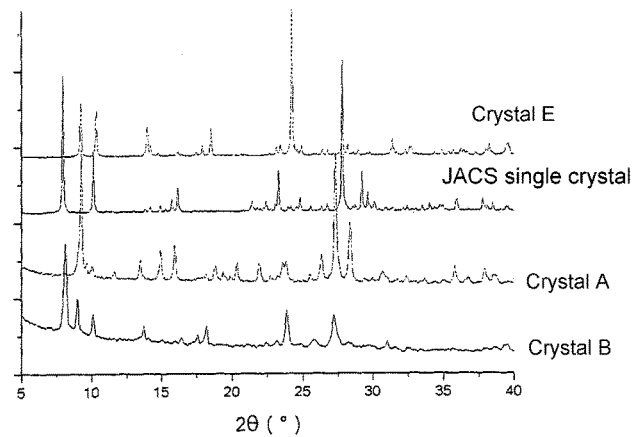
FIG. 20: an overlay of XRPD patterns of crystals, A, B, crystal E and crystal D for comparison.

Comparison of XRPD between the PQQ disodium salt crystals according to the invention and the crystals disclosed in the prior art literatures Crystal E was prepared according to Example 1 in patent literature 1, and compared with crystals A and B according to the invention and the single crystal reported in non-patent literature 1 (JACS, vol. 111, 6822-6828). FIG. 20 shows the graphs comparing these four crystals.

As indicated by this figure, crystalline Form A is apparently different from crystal E at 9.6°, 11.6°, 14.9°, 16.0°, 18.8°, 19.4°, 19.9°, 20.4°, etc. Additionally, the spectra of crystals A and B are also apparently different from that of the JACS single crystal.

Comparative Example 3.

Comparison of DVS and properties between the PQQ disodium salt crystals according to the invention and crystal E As described above, crystal E was prepared according to Example 1 in patent literature 1. The hygroscopic analysis graph of crystal E (shown in FIG. 21) was obtained using the DVS test method and conditions used in the foregoing examples, and its hygroscopic property was compared with those of crystals A and B according to the invention (the results are shown in FIG. 22).

Figure 21:
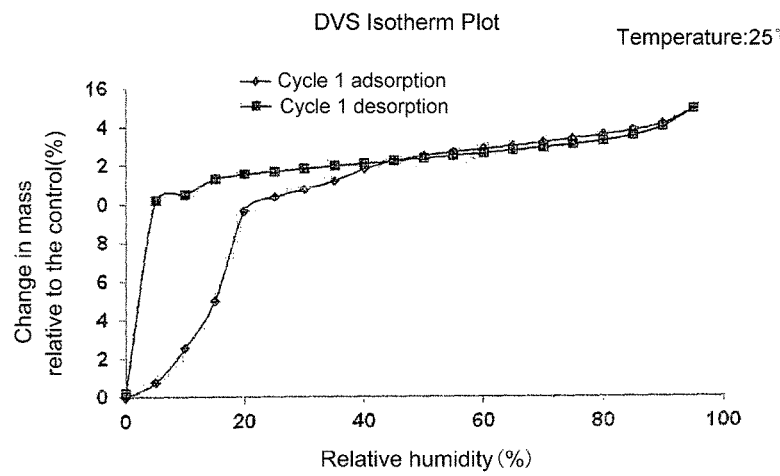
FIG. 21: a hygroscopic analysis (DVS) graph of crystal E.

As seen from FIG. 21, crystal E has certain hygroscopicity. It absorbs 11.8% of moisture at 40% RH, 13.0% at 65% RH, and 13.6% at 80% RH. In a conventional storage environment of 40-80% RH, the variation of hygroscopicity is less than 2%, showing that the crystal is slightly hygroscopic.

Figure 22:
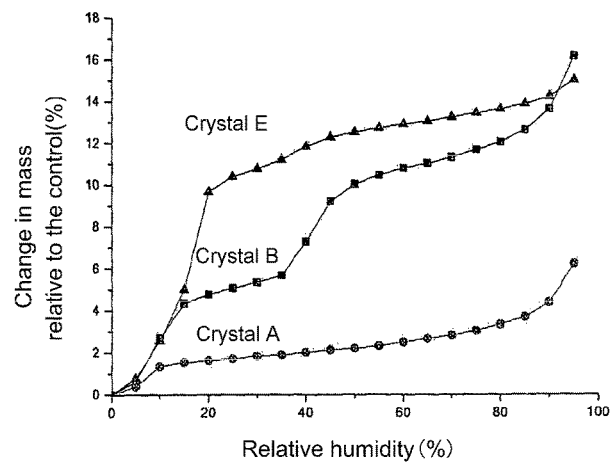
FIG. 22: an overlay of DVS graphs of crystals A, B and crystal E for comparison.

As seen from the comparison indicated in the overlay of DVS graphs in FIG. 22, the three crystal forms are different in hygroscopicity. crystalline Form A, absorbing 3.3% of moisture at 80% RH, shows the smallest hygroscopicity; crystalline Form B, absorbing 12.0% of moisture at 80% RH, shows relatively large hygroscopicity; and crystal E, absorbing 13.6% of moisture at 80% RH, shows the largest hygroscopicity. The hygroscopicity of the crystals according to the invention is superior than crystal E in the prior art, and the properties of crystalline Form A are especially excellent.

The results of the examples show that:

The 2θ values of crystals A and B according to the invention obtained by X-ray powder diffraction using Cu-K α radiation are brand-new, indicating that the crystal forms according to the invention are novel.

In addition, crystals A and B according to the invention have notable advantages in crystallinity, stability, hygroscopicity and processability. Hence, they are expected to be used widely in industry, pharmaceuticals, functional foods, and other fields.

All of the documents mentioned in the invention are incorporated herein by reference, as if each of them were incorporated herein individually by reference. It is to be further understood that various changes or modifications to the invention or recombination of the features described herein can be made by those skilled in the art after reading the above teachings of the invention, and these equivalent variations fall in the scope defined by the accompanying claims of the application as well.

The invention claimed is:

1. A pyrroloquinoline quinone disodium salt crystalline Form A, which shows diffraction peaks at the following 2θ angles in an X-ray powder diffraction pattern obtained by Cu—K α radiation: 9.6±0.2°, 11.6±0.2°, 14.9±0.2°, 16.0±0.2°, 18.8±0.2°, 19.4±0.2°, 20.4±0.2°, 21.9±0.2°, 22.7±0.2°, 23.2±0.2°, 25.6±0.2°, 33.7±0.2°, 35.0±0.2°, 35.8±0.2°, 36.7±0.2°, 38.0±0.2°, and 38.6±0.2°.

2. The disodium salt crystalline Form A of claim 1, wherein said crystalline Form A shows diffraction peaks at the following 2θ angles in an X-ray powder diffraction pattern obtained by Cu—K α radiation: 9.2±0.2°, 9.6±0.2°, 11.6±0.2°, 13.5±0.2°, 14.9±0.2°, 16.0±0.2°, 18.2±0.2 °, 18.8±0.2°, 19.4±0.2°, 20.4±0.2°, 21.9±0.2°, 22.7±0.2°, 23.2±0.2°, 23.8±0.2°, 25.6±0.2°, 26.4±0.2°, 27.3±0.2°, 28.4±0.2°, 30.7±0.2°, 31.7±0.2°, 32.4±0.2°, 33.7±0.2°, 35.0±0.2°, 35.8±0.2°, 36.7±0.2°, 38.0±0.2°, and 38.6±0.2°.

3. The disodium salt crystalline Form A of claim 1, wherein the X-ray powder diffraction pattern of said crystalline Form A obtained by Cu—K α radiation is substantially as shown in FIG. 1.

4. A method for preparing disodium salt crystalline Form A of claim 1, wherein the method is selected from the group consisting of:
(A) suspension crystallization: stirring pyrroloquinoline quinone disodium salt in a solvent to equilibrium at a temperature in the range of 20-60° C. to obtain a suspension, and filtering the suspension to obtain said disodium salt crystalline Form A;
(B) slow volatilization: stirring pyrroloquinoline quinone disodium salt in a solvent, mixing homogeneously to dissolve the salt, and volatizing the solvent at 20-60° C. to obtain said disodium salt crystalline Form A;
(C) anti-solvent precipitation crystallization: dissolving pyrroloquinoline quinone disodium salt in a solvent with high solubility at a temperature in the range of 20-60° C., and adding an anti-solvent with low solubility to the resultant system to precipitate said disodium salt crystalline Form A,
wherein the solubility of the pyrroloquinoline quinone disodium salt in said solvent with high solubility is ≥0.35 g/100 g solvent, and the solubility of the pyrroloquinoline quinone disodium salt in said solvent with low solubility is ≤0.15 g/100 g solvent.

5. The method of claim 4, wherein the solvents used in methods (A) - (C) are selected from the following groups, respectively, in which the ratios are based on volume:
method (A): acetonitrile, methanol, ethanol, water, ethane, heptane, methanol:water, ethanol: water, acetone: water, acetonitrile:water, tetrahydrofuran : water, methanol:hexane, ethanol:hexane, acetonitrile:hexane, tetrahydrofuran:hexane, methanol:methyl tert-butyl ether, ethanol:methyl tert-butyl ether, methanol:toluene, ethanol:toluene, acetonitrile:toluene, methanol:methyl iso-butyl ketone, and toluene:ethane, wherein the volume ratio of the solvents in each mixed solvent is 5:1 to 1:5, preferably 2:1-1:2, more preferably 1:1;
method (B): methanol:water, ethanol:water, isopropanol: water, acetone:water, acetonitrile: water, and tetrahydrofuran:water, wherein the volume ratio of the solvents in each mixed solvent is 10:1 to 1:10, preferably 5:1-1:5;
method (C): the solvent with high solubility is water, and the anti-solvent with low solubility is selected from methanol, ethanol, isopropanol, acetone, acetonitrile and tetrahydrofuran.

6. A composition or packaged product, comprising:
(I) pyrroloquinoline quinone disodium salt crystalline Form A of claim 1, and/or pyrroloquinoline quinone disodium salt crystalline Form A prepared according to the method of claim 4; and
(II) a medically, physiologically or pharmaceutically acceptable carrier and/or excipient.

7. The composition or packaged product of claim 6, wherein the composition or packaged product is selected from the group consisting of: pharmaceutical compositions, functional foods, feedstuffs, additives, microbial inhibitors and preservatives.

* * * * *